(12) United States Patent
Fitzgerald et al.

(10) Patent No.: US 6,528,321 B1
(45) Date of Patent: *Mar. 4, 2003

(54) OPPOSABLE-ELEMENT CHROMATOGRAPHIC ASSAY DEVICE FOR DETECTION OF ANALYTES IN WHOLE BLOOD SAMPLES

(75) Inventors: Daniel Fitzgerald, Campbell, CA (US); Howard M. Chandler, Yarmouth, ME (US); Larry LaPointe, Ryde (AU)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/603,638

(22) Filed: Jun. 26, 2000

(51) Int. Cl.[7] .............................................. G01N 33/53
(52) U.S. Cl. ...................... 436/514; 436/518; 436/524; 436/525; 436/528; 436/531; 436/169; 436/174; 436/805; 436/810; 435/287.1; 435/287.9; 435/805; 435/810; 435/962; 435/970; 422/55; 422/56; 422/58; 422/61
(58) Field of Search ................................. 436/518, 514, 436/524, 525, 528, 531, 169, 174, 805, 810; 435/287.1–287.9, 805, 810, 962, 970; 422/55–61

(56) References Cited

U.S. PATENT DOCUMENTS

| | | | |
|---|---|---|---|
| 4,168,146 A | | 9/1979 | Grubb et al. |
| 4,376,110 A | | 3/1983 | David et al. |
| 4,486,530 A | | 12/1984 | David et al. |
| 4,366,241 A | | 10/1988 | Tom et al. |
| 4,816,224 A | | 3/1989 | Vogel et al. |
| 5,076,925 A | | 12/1991 | Roesink et al. |
| 5,240,862 A | | 8/1993 | Koenhen et al. |
| 5,846,838 A | * | 12/1998 | Chandler |
| 6,087,184 A | * | 7/2000 | Magginetti et al. |

OTHER PUBLICATIONS

Jacques M. Singer, et al., "The Latex Test," American Journal of Medicine, pp. 888–892, Dec. 1956.

* cited by examiner

Primary Examiner—Bao-Thuy L. Nguyen
(74) Attorney, Agent, or Firm—Hogan & Hartson LLP; William H. May; D. David Hill

(57) ABSTRACT

A chromatographic assay device according to the present invention provides a unidirectional immunoassay for an analyte in a whole blood sample with improved sensitivity and freedom from interference. Such a device comprises: (1) a first opposable component including: (a) a sample application zone containing a matrix of porous material permeable to the liquid portion of blood but capable of trapping the cellular components of blood; and (b) a chromatographic medium having first and second ends and including: (i) a detection zone having immobilized thereon a first specific binding partner for the analyte; and (ii) a conjugate zone having a labeled second specific binding partner for the analyte in a resolubilizable form; the sample application zone being in operable contact with the first end of the chromatographic medium and the conjugate zone being located closer to the first end of the chromatographic medium than the detection zone; and (2) a second opposable component including: (a) an applicator; and (b) an absorber. In the device, the first and second opposable components are brought into operable contact to cause the applicator to come into operable contact with the sample application zone to apply a wash liquid thereto and cause the absorber to come into operable contact with the second end of the chromatographic medium. Also within the scope of the invention are multiplex devices that can perform more than one assay simultaneously and test kits.

30 Claims, 3 Drawing Sheets

OPPOSABLE-ELEMENT CHROMATOGRAPHIC ASSAY DEVICE FOR DETECTION OF ANALYTES IN WHOLE BLOOD SAMPLES

BACKGROUND OF THE INVENTION

This invention is directed to assay devices for determination of characteristics of samples, unitized housings, kits incorporating the assay devices, and methods of determining the characteristics of samples using the assay devices.

Among the many analytical systems used for detection or determination of analytes, particularly analytes of biological interest, are chromatographic assay systems. Among the analytes frequently assayed with such systems are:

(1) hormones, such as human chorionic gonadotropin (hCG), frequently assayed as a marker of human pregnancy, as well as luteinizing hormone (LH), follicle stimulating hormone (FSH), and thyroid stimulating hormone (TSH);

(2) antigens, particularly antigens specific to bacterial, viral, and protozoan pathogens, such as Streptococcus, hepatitis virus, and Giardia;

(3) antibodies, particularly antibodies induced as a result of infection with pathogens, such as antibodies to the bacterium Helicobacter pylory and to human immunodeficiency virus (HIV);

(4) other proteins, such as hemoglobin, frequently assayed in determinations of fecal occult blood, an early indicator of gastrointestinal disorders such as colon cancer;

(5) enzymes, such as aspartate aminotransferase, lactate dehydrogenase, alkaline phosphatase, and glutamate dehydrogenase, frequently assayed as indicators of physiological function and tissue damage;

(6) drugs, both therapeutic drugs, such as antibiotics, tranquilizers, and anticonvulsants, and illegal drugs of abuse, such as cocaine, heroin, amphetamines, and marijuana; and (7) vitamins.

Such chromatographic systems are frequently used by physicians and medical technicians for rapid in-office diagnosis or therapeutic monitoring of a variety of conditions and disorders. They are also increasingly used by patients themselves for at-home monitoring of such conditions and disorders.

Among the most important of such systems are the "thin-layer" systems in which a solvent moves across a thin, flat, absorbent medium. Among the most important of tests that can be performed with such thin-layer systems are immunoassays, which depend on the specific interaction between an antigen or hapten and a corresponding antibody or other specific binding partner. The use of immunoassays as a means for testing for the presence or amount of clinically important molecules has been known for some time. As early as 1956, J. M. Singer reported the use of an immune-based latex agglutination test for detecting a factor associated with rheumatoid arthritis (J. M. Singer et al., Am. J. Med., 22:888–892 (1956)).

Among the chromatographic techniques used in conjunction with immunoassays is a procedure known as immunochromatography. In general, this technique uses a disclosing reagent or particle that has been linked to an antibody to the molecule to be assayed, forming a conjugate. This conjugate is then mixed with a specimen and, if the molecule to be assayed is present in the specimen, the disclosing reagent-linked antibodies bind to the molecule to be assayed, thereby giving an indication that the molecule to be assayed is present. The disclosing reagent or particle can be identifiable by color, magnetic properties, radioactivity, enzymatic activity, fluorescence, chemiluminescence, specific reactivity with another molecule, or another physical or chemical property. The specific reactions that are employed vary with the nature of the molecule being assayed and the sample to be tested.

Immunochromatographic assays fall into two principal categories: "sandwich" and "competitive," according to the nature of the antigen-antibody complex to be detected and the sequence of reactions required to produce that complex. In general, the sandwich immunochromatographic procedures call for mixing the sample that may contain the analyte to be assayed with antibodies to the analyte. These antibodies are mobile and typically are linked to a label or disclosing reagent, such as dyed latex, a colloidal metal sol, a nonmetallic colloidal sol, or a radioisotope. This mixture is then applied to a chromatographic medium containing a band or zone. This band or zone contains immobilized antibodies to the analyte of interest. The chromatographic medium is often in the form of a strip resembling a dipstick. When the complex of the molecule to be assayed and the labeled antibody reaches the zone of the immobilized antibodies on the chromatographic medium, binding occurs and the bound labeled antibodies are localized at the zone. This indicates the presence of the molecule to be assayed. This technique can be used to obtain quantitative or semi-quantitative results.

Examples of sandwich immunoassays performed on test strips are described by U.S. Pat. No. 4,168,146 to Grubb et al. and U.S. Pat. No. 4,366,241 to Tom et al., both of which are incorporated herein by this reference.

In a competitive immunoassay, typically, a labeled analyte or analogue is supplied, and a competitive reaction is set up between the unlabeled analyte in the sample and the labeled analyte or analogue for binding to an immobilized specific binding partner on the test strip. In general, competitive immunoassays are more suitable for assay of haptens, because they do not require the formation of a ternary sandwich complex.

Although useful, currently available chromatographic techniques using test strips have a number of drawbacks. Many samples, such as fecal samples, contain particulate matter that can clog the pores of the chromatographic medium, greatly hindering the immunochromatographic process. Other samples, such as blood, contain cells and colored components that make it difficult to read the results of the tests. Even if the sample does not create interference, it is frequently difficult with existing chromatographic test devices to apply the sample to the chromatographic medium so that the sample front moves uniformly through the chromatographic medium to ensure that the sample reaches the area where the binding is to occur in a uniform, straight-line manner.

Sample preparation and waste generation are responsible for other problems with currently available devices and techniques for immunochromatography. The increased prevalence of diseases spread by infected blood and blood fractions, such as AIDS and hepatitis, has exacerbated these problems. It is rarely possible to apply a sample (such as blood or feces) or a sampling device (such as a throat swab) directly to the chromatographic medium. Several extraction and pretreatment reactions are usually required before the sample can be applied to the chromatographic medium. These reactions are typically carried out by the physician or technician performing the test in several small vessels, such as test tubes or microfuge tubes, requiring the use of transfer devices such as pipettes. Each of these devices is then contaminated and must be disposed of using special precautions so that workers or people who might inadvertently come into contact with the waste do not become contaminated and subject to infection by infectious agents contained in the waste.

When blood samples are involved, there are additional considerations. Whole blood samples are most easily accommodated by the reverse flow format, i.e., one that performs bidirectional chromatography. The reverse-flow format has the advantage of allowing the test results to be read against the clear white or translucent chromatographic medium, eliminating the potential for obscuring weak test results. However, in a such a reverse-flow format, the amount of sample that is brought into contact with the capture line or detection zone is very limited. In a typical assay, approximately only 3–5 µl of the applied sample is utilized, and hence assay sensitivity is "capture limited." This is especially true if the immunological reagents used are of low affinity or avidity for the performance of immunochromatographic assays. Therefore, it would be desirable to have an immunochromatographic assay device that could perform assays for analytes found in blood with a unidirectional assay format so that the sensitivity of the assay could be increased.

Additionally, such a device should be capable of receiving a possibly contaminated sample or a sample preparation device directly so as to eliminate the need for extraction vessels and transfer devices. Such a device, preferably in the form of a test strip, should also be capable of performing immunochromatographic assays on colored samples or samples containing particulates without interference and should be able to deliver the sample to the chromatographic medium uniformly and evenly to improve accuracy and precision of the test. This aspect of an improved assay device is particularly important in avoiding false negatives and false positives. In particular, an improved assay device should also be capable of performing a unidirectional assay on whole blood samples.

Another aspect in which present immunochromatographic test devices need improvement is in reducing the volume of sample required to achieve the threshold sensitivity of the analyte to be determined. This is particularly important if the sample is whole blood and the donor is an infant, patient suffering from blood loss or anemia pediatric patient, or geriatric patient, limiting the volume of blood that can be drawn. If multiple tests are to be performed, as is often the case, it is crucial that the minimum volume of blood be used for each test.

Another improvement in immunochromatographic assay test devices and formats is related to the use of monoclonal antibodies in assay test formats, particularly for assay of hCG and related hormones such as LH, FSH, and TSH. Although monoclonal antibodies can yield an increase in sensitivity and specificity for such assays, they can cause additional problems, particularly when murine monoclonal antibodies are used. If a plasma or serum sample is used, the human-anti-murine antibody (HAMA) response can cause interference in the assay when monoclonal antibodies are used. Therefore, there is a need to control and monitor the existence of such interference and provide an indication to the user that such interference does not exist in a particular assay.

Accordingly, there is a need for an improved immunochromatographic assay device that can perform unidirectional assays with blood samples and that can provide a high degree of sensitivity and reproducibility in a unidirectional immunochromatography format.

SUMMARY

A chromatographic assay device according to the present invention meets these needs and provides a unidirectional immunoassay for an analyte in a blood sample while preventing interference from blood cells and colored components. The ability to perform a unidirectional immunoassay for an analyte in a blood sample provides improved sensitivity for detection of analytes such as hormones.

An embodiment of a chromatographic immunoassay device according to the present invention comprises:
(1) a first opposable component including:
   (a) a sample application zone containing a matrix of porous material permeable to the liquid portion of blood but capable of trapping the cellular components of blood; and
   (b) a chromatographic medium having first and second ends and including:
      (i) a detection zone having immobilized thereon a first specific binding partner for the analyte; and
      (ii) a conjugate zone having a labeled second specific binding partner for the analyte in a resolubilizable form; the sample application zone being in operable contact with the first end of the chromatographic medium and the conjugate zone being located closer to the first end of the chromatographic medium than the detection zone; and
(2) a second opposable component including:
   (a) an applicator; and
   (b) an absorber.

In this device, the first and second opposable components are brought into operable contact to cause the applicator to come into operable contact with the sample application zone to apply a wash liquid thereto and to cause the absorber to come into operable contact with the second end of the chromatographic medium.

Typically, the label is a colloidal particle label. Preferably, the colloidal particle label is a colloidal carbon label. Typically, the label is a visibly detectable label.

The analyte can be selected from the group consisting of human chorionic gonadotropin (hCG), luteinizing hormone (LH), follicle stimulating hormone (FSH), thyroid stimulating hormone (TSH), corticotropin-releasing hormone (CRH), growth hormone-releasing hormone (GHRH), prolactin, human growth hormone (hGH), β-lipotropin, corticotropin, β-endorphin, calcitonin, parathormone, human placental lactogen (hPL), insulin, glucagon, pancreatic polypeptide (PP), secretin, cholecystokinin-pancreozyrnin, motilin, vasoactive intestinal peptide, gastric inhibitory peptide, and erythropoietin. Particularly significant analytes include human chorionic gonadotropin (hCG), luteinizing hormone (LH), follicle stimulating hormone (FSH), and thyroid stimulating hormone (TSH).

When the analyte is hCG, typically the first specific binding partner is a monoclonal antibody specific for the α subunit of hCG and the second specific binding partner is a monoclonal antibody specific for the β subunit of hCG and not cross-reactive with luteinizing hormone. Alternative arrangements of monoclonal antibodies can also be used, such as having the first specific binding partner being a monoclonal antibody specific for the β subunit of hCG and the second specific binding partner being specific for the cc subunit of hCG.

Preferably, the device further comprises a barrier to prevent fluid now between the second applicator and the sample application zone.

Preferably, the matrix contains a detergent and a chelating agent. The detergent can be a polyoxyethylene sorbitan monolaurate, a polyoxyethylene sorbitan monooleate, a polyoxyethylene sorbitan monopalmitate, a polyoxyethylene sorbitan monostearate, a polyoxyethylene sorbitan trioleate, a polyethylene glycol fatty alcohol ether, a polyoxyethylene fatty acid ester, or a polyoxyethylene ether. Most preferably, the detergent is a polyoxyethylene sorbitan monolaurate.

The chelating agent can be EDTA or EGTA. Preferably, the chelating agent is EDTA.

In the device, the chromatographic medium can further include a control zone separate from the detection zone. The control zone can include an analyte or an analyte analogue immobilized thereto. Alternatively, the control zone can include an immobilized third specific binding partner that does not bind the analyte but does specifically bind the labeled second specific binding partner.

Another aspect of the present invention is a test kit. The test kit comprises, packaged in separate containers:

(1) the chromatographic assay device described above-;.and (2) a wash liquid for application to the second applicator of the assay device.

Another aspect of the present invention is a method for detecting or determining an analyte in a test sample comprising the steps of:

(1) applying a test sample to the sample application zone of the chromatographic assay device described above;

(2) applying a wash liquid to the applicator of the chromatographic assay device;

(3) allowing the sample to migrate from the sample application zone through the chromatographic medium including the conjugate zone and the detection zone to resolubilize the labeled first specific binding partner;

(4) bringing the first and second opposable components into operable contact to apply the wash liquid to the sample application zone;

(5) allowing the wash liquid to move through at least a portion of the chromatographic medium including the detection zone; and (6) observing or measuring the labeled second specific binding partner for the analyte at the detection zone in order to detect or determine the analyte.

Another aspect of the present invention is a multiplex device capable of performing more than one assay in the same device. The device comprises:

(1) a first opposable component including:
  (a) at least two sample application zones, one for each assay that can be performed in the device, each sample application zone containing a matrix of porous material permeable to the liquid portion of blood but capable of trapping the cellular components of blood, the sample application zones being laterally spaced on the first opposable component; and
  (b) at least two chromatographic media, one for each sample application zone, each chromatographic medium having first and second ends and including:
    (i) a detection zone having immobilized thereon a first specific binding partner for the analyte; and
    (ii) a conjugate zone having a labeled second specific binding partner for the analyte in resolubizable form, each sample application zone being in operable contact with the first end of one of the chromatographic media and each conjugate zone being located closer to the first end of each chromatographic medium than each detection zone is located; and (1) a second opposable component including:
  (a) at least two applicators, one for each chromatographic medium; and
  (b) at least two absorbers, one for each chromatographic medium.

In the multiplex version of the device, the first and second opposable components are brought into operable contact to cause each applicator to come into operable contact with the corresponding sample application zone to apply a wash liquid thereto and cause each absorber to come into operable contact with the second end of the corresponding chromatographic medium.

Each of the immobilized specific binding partners on the chromatographic media can bind the same analyte. In this alternative, the multiplex assay device performs a number of tests for the same analyte. Alternatively, each of the immobilized specific binding partners on the chromatographic media can bind a different analyte. In this alternative, the multiplex assay device performs tests for a number of different analytes.

Typically, each of the labels of the labeled specific binding powers is the same.

Preferably, the device further comprises at least two barriers to prevent fluid flow between each second applicator and each sample application zone, a barrier being located between each second applicator and each sample application zone.

Preferably, each matrix contains a detergent and a chelating agent, as described above.

Each chromatographic medium can further include a control zone separate from the detection zone. Preferably, each control zone includes analyte immobilized thereto, the analyte being the same analyte as bound by the immobilized first specific binding partner on each chromatographic medium.

Another aspect of the present invention is a test kit incorporating the multiplex assay device of the present invention. The test kit comprises, packaged in separate containers:

(1) the multiplex chromatographic assay device described above; and (2) a wash liquid for application to each second applicator of the assay device.

Another aspect of the present invention is a method for detecting or determining at least one analyte in at least one test sample comprising the steps of:

(1) applying a test sample to at least one of the sample application zones of the multiplex chromatographic assay device described above;

(2) applying a wash liquid to at least one of the applicators of the chromatographic assay device;

(3) allowing the sample to migrate from the sample application zone through the corresponding chromatographic medium including the conjugate zone and the detection zone to resolubilize the labeled first specific binding partner;

(4) bringing the first and second opposable components into operable contact to apply the wash liquid to the sample application zone;

(5allowing the wash liquid to move through at least a portion of the corresponding chromatographic medium including the detection zone; and (6 observing or measuring the labeled second specific binding partner for the at least one analyte at the detection zone in order to detect or determine the analyte.

Another embodiment of an assay device according to the present invention employs additional specific binding partners to prevent or detect possible interference by a human anti-murine antibody (HAMA) response occurring in a test subject. One of these specific binding partners acts to scavenge antibodies in the test sample that would otherwise bind to the immobilized specific binding partner for the analyte or the mobile labeled specific binding partner for the analyte.

One version of this embodiment comprises:

(1) a first opposable component including:
  (a) a sample application zone containing a matrix of porous material permeable to the liquid portion of blood but capable of trapping the cellular components of blood; and
  (b) a chromatographic medium having first and second ends and including:
    (i) a detection zone having immobilized thereon a first specific binding partner, the first specific binding partner binding the analyte;
    (ii) a conjugate zone having a labeled second specific binding partner in a resolubilizable form, the second specific binding partner binding the analyte;
    (iii) a capture zone having thereon a third specific binding partner, the third specific binding partner binding human antibodies that bind the first or second specific binding partners; and;
    (iv) a validation zone having immobilized thereon a fourth specific binding partner, the fourth specific binding partner binding human antibodies that bind the first or second specific binding partners;
(2) a second opposable component including:
  (a) an applicator; and
  (b) an absorber.

In this embodiment, the sample application zone is in operable contact with the first end of the chromatographic medium, the conjugate zone is located closer to the first end of the chromatographic medium than the detection zone, the capture zone is located closer to the first end of the chromatographic medium than the conjugate zone, and the validation zone is located closer to the second end of the chromatographic medium than the detection zone.

The first and second opposable components are brought into operable contact to cause the applicator to come into operable contact with the sample application zone to apply a wash liquid thereto and cause the absorber to come into operable contact with the second end of the chromatographic medium.

Another version of this embodiment comprises:

(1) a first opposable component including:
  (a) a sample application zone containing a matrix of porous material permeable to the liquid portion of blood but capable of trapping the cellular components of blood, the sample application zone further containing a first specific binding partner; and
  (b) a chromatographic medium having first and second ends and including:
    (i) a detection zone having immobilized thereon a second specific binding partner, the second specific binding partner specifically binding the analyte;
    (ii) a conjugate zone having a labeled third specific binding partner in a resolubilizable form, the third specific binding partner specifically binding the analyte; and;
    (iii) a validation zone having immobilized thereon a fourth specific binding partner, the fourth specific binding partner binding human antibodies that bind the second or third specific binding partners;
(1) a second opposable component including:
  (a) an applicator; and
  (b) an absorber.

In this version of the embodiment, the sample application zone is in operable contact with the first end of the chromatographic medium, the conjugate zone is located closer to the first end of the chromatographic medium than the detection zone, and the validation zone is located closer to the second end of the chromatographic medium than the detection zone. The first specific binding partner at the sample application zone binds human antibodies that bind the second or third specific binding partners. The first and second opposable components are brought into operable contact to cause the applicator to come into operable contact with the sample application zone to apply a wash liquid thereto and cause the absorber to come into operable contact with the second end of the chromatographic medium.

A third version of this embodiment of the present invention comprises:

(1) a first opposable component including:
  (a) a sample application zone containing a matrix of porous material permeable to the liquid portion of blood but capable of trapping the cellular components of blood;
  (b) a conductor containing a first specific binding partner; and
  (c) a chromatographic medium having first and second ends and including:
    (i) a detection zone having immobilized thereon a second specific binding partner, the second specific binding partner binding the analyte;
    (ii) a conjugate zone having a labeled third specific binding partner in a resolubilizable form, the third specific binding partner binding the analyte; and
    (iii) a validation zone having immobilized thereon a fourth specific binding partner that binds human antibodies that bind the second or third specific binding partners;
(1) a second opposable component including:
  (a) an applicator; and
  (b) an absorber.

In this embodiment, the first specific binding partner binds human antibodies that bind the second or third specific binding partners. The sample application zone is in operable contact with the conductor and the conductor is in operable contact with the first end of the chromatographic medium. The conjugate zone is located closer to the first end of the chromatographic medium than the detection zone, and the validation zone is located closer to the second end of the chromatographic medium than the detection zone. The first and second opposable components are brought into operable contact to cause the applicator to come into operable contact with the sample application zone to apply a wash liquid thereto and cause the absorber to come into operable contact with the second end of the chromatographic medium.

The present invention also encompasses test kits incorporating these versions of this embodiment and assay methods employing these versions.

BRIEF DESCRIPTION OF THE DRAWINGS

These and other features, aspects, and advantages of the present invention will become better understood with reference to the following description, appended claims, and accompanying drawings where:

DESCRIPTION

Definitions

Figure 1:
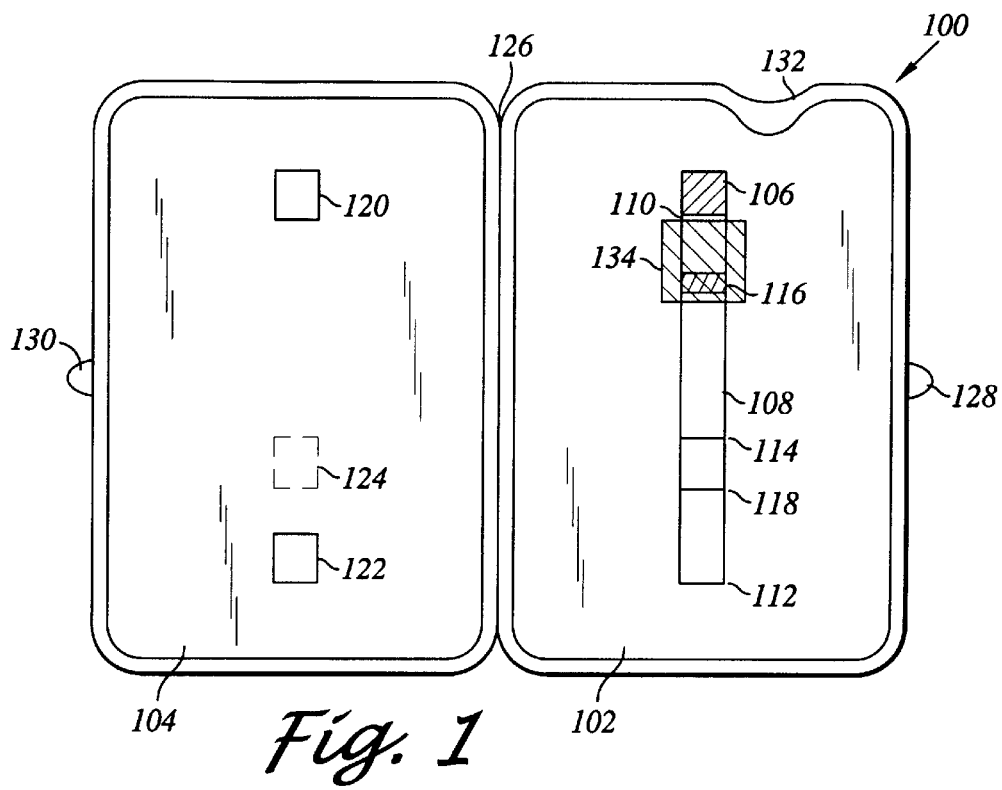
FIG. 1 is a drawing of an assay device according to the present invention particularly intended for use with a whole blood sample.

In the context of this disclosure, the following terms are defined as follows unless otherwise indicated:

Specific binding partner: A member of a pair of molecules that interact by means of specific noncovalent interactions that depend on the three-dimensional structures of the molecules involved. Typical pairs of specific binding partners include antigen-antibody, hapten-antibody, hormone-receptor, nucleic acid strand-complementary nucleic acid strand, nucleic acid strand-sequence-specific nucleic acid binding protein, substrate-enzyme, inhibitor-enzyme, carbohydrate-lectin, biotin-avidin, and virus-cellular receptor.

Operable contact: Two solid components are in operable contact when they are in contact, either directly or indirectly, in such a manner that a liquid can flow from one of the two components to the other substantially uninterruptedly, by capillarity or otherwise. "Direct contact" means the two elements are in physical contact, such as edge-to-edge or front-to-back. "Indirect contact" means the two elements are not in physical contact, but are bridged by one or more conducting means. This bridging by one or more conducting means can be either edge-to-edge or front-to-back, such as by the opposition or bringing into contact of planar elements.

Analyte: The term "analyte" includes both the actual molecule to be assayed and analogues and derivatives thereof when such analogues and derivatives bind another molecule used in the assay in a manner substantially equivalent to that of the analyte itself.

Antibody: The term "antibody" includes both intact antibody molecules of the appropriate specificity and antibody fragments (including Fab, F(ab'), F(ab')$_2$, and Fv fragments), as well as chemically modified intact antibody molecules and antibody fragments, including hybrid molecules assembled by in vitro reassociation of subunits. Also included are genetically engineered antibodies of the appropriate specificity, including single-chain derivatives. Both polyclonal and monoclonal antibodies are included unless otherwise specified.

Label: The term "label" is used herein to refer to any directly or indirectly detectable or determinable moiety that is covalently or noncovalently associated with a specific binding partner that binds one or more specific binding partners and participates in an assay performed by a device according to the present invention. Typically "label" is used to refer only to the detectable or determinable moiety itself. The term "labeled specific binding partner" is used to refer to the covalent conjugate or noncovalent complex of the label and the specific binding partner. Labels used for the devices according to the present invention are described below.

Secondary specific binding partner: The term "secondary specific binding partner" is used to designate an additional specific binding partner that binds to a member of a pair of specific binding partners when the pair of specific binding partners is interacting. For example, a pair of specific binding partners can comprise Giardia antigen and rabbit anti-Giardia antibody. In that case, the secondary specific binding partner can be goat anti-rabbit IgG antibody. The secondary specific binding partner can be specific for the species, class, or subclass of an antibody specific binding partner to which it binds. Alternatively, when one of the specific binding partners is labeled with biotin, the secondary specific binding partner can comprise a molecule conjugated to avidin or streptavidin.

Sample: The term "sample" as used herein, refers to any fluid that can be applied to the assay device, directly or indirectly and that contains or may contain an analyte, including, but not limited to, serum, plasma, whole blood, saliva, urine, cerebrospinal fluid, fecal extracts, material contained in a swap such as a throat swab, or other fluids.

Interference: The term "interference" as used herein in conjunction with reference to the human anti-murine antibody (HAMA) response, refers to either the existence of false negative or false positive results that would be caused by the presence of HAMA in a sample of human origin.

I. CHROMATOGRAPHIC ASSAY DEVICES

One aspect of the present invention comprises chromatographic assay devices particularly useful for the assay of analytes in biological samples, particularly whole blood samples. These devices are suitable for the direct application of biological samples, particularly whole blood samples, without preliminary extraction steps, and are constructed so as to minimize interference with assay results caused by particulates or colored samples. These devices are intended to provided more homogeneous mixing of the analyte and a labeled specific binding partner that is typically in resolubilizable form.

The device has at least two opposable components, typically substantially planar. One of these substantially planar components has on its surface a chromatographic medium. When there are two opposable components, one of the opposable components is designated the first opposable component and the other is designated the second opposable component. Typically, the first opposable component is the component with the chromatographic medium. This distinction is arbitrary and for convenience in description; the role of each of the opposable components is determined by the element or elements located on it.

The device also has means for opposing the opposable components, also referred to as bringing them into operable contact, and applying pressure thereto. The opposable components can be brought into opposition from a position in which they are not in opposition by direct manual closure, i.e., by manipulation by the operator. The pressure applied is sufficient to transfer fluid from one opposable component to another opposable component in a direction substantially normal to the opposable components in a sequence determined by the construction of the assay device. The end result is that the sample is applied to the chromatographic medium for detection or determination of the analyte thereon. The pressure also drives the fluid through the chromatographic medium to accelerate the process of chromatography, giving a detectable result in less time. Additionally, the pressure makes possible the performance of steps, such as extraction steps, in the device, and can be used to remove excess fluid from the chromatographic medium by absorbers to reduce the background of the assays. The pressure is generated by placing the opposable components into opposition and maintained by holding the components in opposition by engagers such as locks or clasps or, alternatively, by an adhesive strip along the outside margin of one of the components that allows sealing the components.

Devices according to the present invention can be constructed for the performance of either a sandwich or a competitive assay. However, devices according to the present invention are particularly useful for sandwich immunoassays. As used herein, the term "immunoassay" is used generally to include specific binding assays and need not necessarily be restricted to assays in which any or all of the specific binding partners are antibodies, unless so specified.

The degree of pressure employed in the device can be regulated so that it is optimum for the characteristics of the chromatographic medium, analyte, and label.

Assay methods using a device according to the present invention can give a qualitative, semi-quantitative, or quantitative indication of analyte presence or concentration, depending upon the concentration of the labeled specific binding partner at the detection zone and the size of the detection zone, as well as the detection method used. In general, in the specification, the term "detect" is used to refer to a qualitative indication of the presence or absence of an analyte, while the term "determine" is used to refer to either a semi-quantitative or a quantitative determination of the concentration of the analyte. The term "observe" is typically used to refer to a visual observation leading to a qualitative or semi-quantitative determination or detection of analyte presence or concentration, while the term "measure" is typically used to refer to an instrumental measurement that yields a quantitative determination of analyte concentration. Such a measurement is typically by spectroscopy, although other methods can be used.

A. Elements Common to Devices According to the Present Invention

A number of elements are common to assay devices according to the present invention and are discussed here for convenience.

1. The Chromatographic Medium

The chromatographic medium is typically a strip. Typically, the strip is substantially planar, although this is not required in all applications. It is typically rectangular, having first and second ends and first and second surfaces. Throughout this description, the term "first end" refers to the end at or near which liquid is applied to the chromatographic medium and the term "second end" applies to the opposite end of the chromatographic medium. Liquid applied at or near the first end of the chromatographic medium can be, but is not necessarily, a sample or a treated sample, and can contain a resolubilized labeled specific binding partner for the analyte.

Alternatively, as indicated below, the chromatographic medium can contain a zone of resolubilizable labeled specific binding partner for the analyte in a zone referred to as a "conjugate zone."

The chromatographic medium is composed of material suitable as a medium for thin-layer chromatography of analyte and analyte-antibody conjugates, such as nitrocellulose, cellulose acetate, derivatives of nitrocellulose or cellulose acetate, cellulose, nylon, rayon, paper, or silica. Preferably, particularly when a conjugate zone is located on the chromatographic medium, the chromatographic medium is nitrocellulose. The chromatographic medium can be pretreated or modified as needed. Typically, the chromatographic medium is translucent, so that the colored zones appearing on it can be viewed from either side, such as through an aperture.

2. Absorbers

In a number of devices according to the present invention, absorbers can be brought into operable contact with at least one end of the chromatographic medium. The absorbers can be made of any bibulous material that will hold a liquid sufficiently so that liquid can be drawn through the chromatographic medium and accumulated in the absorber. Typical materials for the absorber include, but are not limited to, filter paper. The size and shape of the absorber can be chosen according to the volume of fluid used in the assay.

3. Other Fluid-Carrying Elements

As described below, in particular devices according to the present invention, other fluid-carrying elements can be employed as sample application zones, capture zones, applicators, or conductors. These elements are typically prepared of hydrophilic media that pass liquids without substantially absorbing them. Such materials are well known in the art. These materials include nonwoven polyester and extruded cellulose acetate. In some cases, these elements can have incorporated therein a component in dry form that can be resolubilized by addition of a liquid to the element, typically an aqueous liquid. The terms "resolubilized," "resolubilizable," and similar terminology are used herein generally to refer to the state of such components.

4. Opposable Components

Many of the embodiments of the assay device according to the present invention comprise two opposable components. The bodies of the opposable components are preferably made of laminated cardboard that is sufficiently impervious to moisture to contain liquids involved in the performance of the assay carried out by the device. Other cellulose-based materials, such as paperboard or solid bleached sulfite (SBS) can also be used. Alternatively, the bodies of the opposable components can be made of plastic that is impervious to moisture. A suitable plastic is polycarbonate plastic such as Lexan™

The opposable components are joined by a hinge, preferably made of a material impermeable to liquids, such as a plastic that can be compatibly joined with or is the same as the material used for the first and second opposable components.

5. Labeled Components

For assay devices intended to perform a sandwich immunoassay, the labeled component is typically a labeled specific binding partner to the analyte. This labeled component is typically mobile, in that it can migrate through the chromatographic medium, whether free or bound to analyte. The label is preferably a visually detectable label, such as a colloidal label. The colloidal label can either be a colloidal metal label or a non-metallic colloidal label.

A preferred non-metallic colloidal label is colloidal carbon. Colloidal carbon labels for labeling of specific binding partners are described, for example, in U.S. Pat. No. 5,529, 901 to Van Doom et al., incorporated by this reference. In general, a suitable colloidal carbon label is prepared from carbon black powder charcoal of the appropriate grade.

Suitable carbon black powder charcoal is an amorphous black solid in the form of a fine powder with no odor, has a melting point of 3000° C., has a specific gravity of 1.7 to 1.9, has a pH greater than 7 when measured with 50 grams in 1 liter of water, and has a particle size of 25 nm. Additionally, it is strongly preferred that such carbon powder produce a carbon sol in an aqueous medium, such as pure water or a buffer system of low ionic strength, that does not require an added stabilizing agent to be stable. The stability of carbon sols in the absence of added stabilizing agent can be predicted on the basis of three properties of the carbon particles: the dibutylphthalate adsorption, the volatile content, and the average primary particle diameter.

From these particles, carbon sots can be prepared by a variety of techniques, including ultrasonification, shaking or boiling (with or without stirring) a mixture of carbon particles and an aqueous medium without stabilizing agents.

Specific binding partners such as antibodies can be bound to carbon sols by noncovalent interactions. Although Applicants do not intend to be bound by this theory, it is likely that the noncovalent interactions involve hydrophobic interactions between the specific binding partner and the carbon sol.

Sonification of carbon powder in pure water or in a buffer of low ionic strength, followed by mixing the colloidal carbon suspension with a suspension of a macromolecule such as a specific binding partner, i.e., an antibody, in the same buffer under gentle mixing, results in conjugates of the specific binding partner with the carbon sol label suitable for use with immunoassay devices according to the present invention.

Alternatively, addition of a suspension of a macromolecular specific binding partner in a buffer of low ionic strength, with the final macromolecular concentration at the minimal protective amount, to a mixture of carbon powder and water during a short homogenization step by sonification leads to the formation of conjugates of the specific binding partner with the carbon sol label.

If a colloidal metal label is used, preferably, the colloidal metal label is gold, silver, bronze, iron, or tin; most preferably, it is gold. The preparation of gold labeled antibodies and antigens is described in J. DeMey, "The Preparation and Use of Gold Probes" in *Immunocytochemistry: Modern Methods and Applications* (J. M. Polak & S. VanNoorden, eds., Wright, Bristol, England, 1986), ch. 8 pp. 115–145, incorporated herein by this reference. Antibodies labeled with colloidal gold are commercially available, such as from Sigma Chemical Company, St. Louis, Mo.

Alternatively, still other colloidal labels, such as a colloidal sulfur label or a dye-silica label, can also be used.

In a less preferred alternative, the visually detectable label can be a colored latex label. It is also possible to use other labels, such as a radioactive label, a fluorescent label, a chemiluminescent label, a bioluminescent label, or an enzyme label. The use of these labels is well known in the art and need not be detailed further here.

Typically, the resolubilizable labeled specific binding partner is located either in a conjugate pad or is dried down directly on the chromatographic medium, preferably a nitrocellulose medium. If a conjugate pad is used, the conjugate pad is a fluid-carrying element of the type described above.

Alternatively, and preferably, the resolubilizable labeled specific binding partner is dried down directly on a nitrocellulose chromatographic medium. This is particularly useful for a colloidal carbon label.

In general, the process for directly drying down labeled specific binding partners on a nitrocellulose chromatographic medium comprises:

(1) diluting a solution of the labeled specific binding partner into a diluent containing a stabilizing protein, a stabilizing carbohydrate, and an ionic buffer;

(2) placing the diluted labeled specific binding partner on the nitrocellulose chromatographic medium;

(3) heating the nitrocellulose chromatographic medium with the labeled specific binding partner; and (4) placing the nitrocellulose chromatographic medium with the labeled specific binding partner under a vacuum to produce a stabilized resolubilizable labeled specific binding partner on the nitrocellulose chromatographic medium.

The stabilizing protein is a protein that is readily soluble, does not specifically bind either the specific binding partner or any molecule bound by the specific binding partner, and lacks enzymatic activity that catalyzes a reaction involving any component that is a participant in the assay carried out by a device of which the nitrocellulose solid support is a part. Preferably, the stabilizing protein is a globular protein, such as casein, serum albumin, ovalbumin, lactalbumin, grain albumin, or soybean albumin. A particularly preferred stabilizing protein is casein. Preferably, the concentration of stabilizing protein in the diluent is about 2.0% to about 3.0%, more preferably about 2.2% to about 2.8%, most preferably about 2.5%. A particularly preferred concentration of casein is about 2.5% in the diluent.

The stabilizing carbohydrate is any carbohydrate that is readily soluble and does not interact either with the labeled specific binding partner or with the nitrocellulose chromatographic medium. The stabilizing carbohydrate can be lactose, sucrose, dextran, mannose, glucose, galactose, maltose, or another monosaccharide, disaccharide, oligosaccharide, or polysaccharide. A particularly preferred stabilizing carbohydrate is sucrose. A preferred concentration of stabilizing carbohydrate is from about 6% to about 10% in the diluent, more preferably from about 7% to about 9% in the diluent, most preferably about 8% in the diluent. A particularly preferred concentration of sucrose as a stabilizing carbohydrate is about 8% in the diluent.

The ionic buffer is any buffer that does not interact either with the labeled specific binding partner or with the nitrocellulose chromatographic medium and that provides sufficient buffering capacity at physiological pH to prevent a change in the pH by more than about 0.1 unit during the preparation of the chromatographic medium. As used herein, the term "ionic" also includes zwitterionic buffers. The pH of the buffer is preferably from about 6.5 to about 8.5, more preferably from about 7.0 to about 8.0, most preferably about 7.5. The buffer can be a buffer such as a phosphate buffer, a citrate buffer, a N-(2-acetamido)iminodiacetic acid (ADA) buffer, a piperazine-N,N'-bis(2-ethanesulfonic acid) (PIPES) buffer, a 3-(N-morpholino)propanesulfonic acid (MOPS) buffer, a N-2-hydroxyethylpiperazine-N'-2-ethanesulfonicacid (HEPES) buffer, a N-2-hydroxyethylpiperazine-N'-3-propanesulfonic acid (HEPPS) buffer, a N[tris(hydroxymethyl)methyl]glycine (Tricine) buffer, a tris(hydroxyaminomethyl)methane (Tris buffer), a glycylglycine buffer, or a N,N-bis(2-hydroxyethyl) glycine (Bicine) buffer. Other buffers are known in the art. A particularly preferred buffer is 5 mM potassium phosphate, pH 7.5.

One particularly preferred method of drying down a resolubilizable colloidal carbon labeled specific binding partner is to dilute a stock solution of the labeled specific binding partner in 5 mM potassium phosphate, pH 7.5, with 2 volumes of diluent (2.5% casein, 5 mM potassium phosphate, pH 7.5, 8% sucrose), stripe the diluted labeled specific binding partner on the chromatographic medium using a striping system at 4.2 µl/sec at a platform speed of 51 mm/sec, place the striped chromatographic medium in a 42° C. incubator for 20 minutes, then place the chromatographic medium in a vacuum chamber overnight under ambient temperature. This procedure results in the formation of a chromatographic medium with a resolubilizable labeled specific binding partner on the medium in a conjugate zone.

B. Device for Assay of Whole Blood Sample with Coniugate Zone on Chromatographic Medium An embodiment of an assay device according to the present invention has the resolubilizable labeled specific binding partner for the analyte in a conjugate zone on the chromatographic medium. This embodiment of the assay device is particularly suited for assay of an analyte in a whole blood sample and provides a wash.

This device is shown in FIG. 1. The specific binding partners used in this device are as follows: (1) a first specific binding partner specifically binding the analyte, which is immobilized in a detection zone; (2) a second specific binding partner specifically binding the analyte, which is in resolubilizable form in a conjugate zone; (3) optionally, a third specific binding partner specific for the second labeled specific binding partner but that does not bind the analyte, immobilized in a control zone. The third specific binding partner can be replaced by analyte or analyte analogue.

The device 100 includes a first opposable component 102 and a second opposable component 104. The first opposable component 102 has a sample application zone 106 that contains a matrix of porous material permeable to the liquid portion of blood but capable of trapping the cellular components of blood. The first opposable component 102 also includes a chromatographic medium 108 having a first end 110 and a second end 112. The chromatographic medium 108 includes a detection zone 114, a conjugate zone 116, and optionally a control zone 118. These zones are located on the chromatographic medium 108 so that the conjugate zone 116 is located closer to the first end 110 of the chromatographic medium 108 than is the detection zone 114. The control zone 118, if present, is located furthest from the first end 110 and closest to the second end 112 of the chromatographic medium 108 of the three zones.

The detection zone 114 contains a first immobilized specific binding partner for the analyte. The conjugate zone 116 contains a second labeled specific binding partner for the analyte in resolubilizable form. The control zone 118 contains a third specific binding partner specific for the second labeled specific binding partner but that does not bind the analyte. Alternatively, the control zone 118 can contain immobilized analyte or analyte analogue. Analyte analogues include, but are not limited to, the analyte stably covalently or noncovalently attached to a protein or another molecule that is, in turn, attached to the chromatographic medium. The analyte analogue can include a spacer. Typically, if a spacer is used, it includes saturated hydrocarbon moieties, but oxygen and nitrogen atoms as well as unsaturated hydrocarbon moieties can also be included. Typically, the spacer is about 10 Å to about 30 Å in length, but other lengths can be used. Methods of immobilization of both macromolecules and small molecules to solid supports are well known in the art and are described, for example, in G. T. Hermanson et al., "immobilized Affinity Ligand Techniques" (Academic Press, Inc., San Diego, 1992), incorporated herein by this reference.

As detailed below, the labeled specific binding partner in the conjugate zone 116 and the unlabeled immobilized specific binding partner in the detection zone 114 can be the same or can be different, depending on the analyte being assayed and the nature of the available specific binding partners.

The sample application zone 106 is in operable contact with the first end 110 of the chromatographic medium 108. The operable contact between the first end 110 of the chromatographic medium 108 and the sample application zone 106 can be direct contact or can be contact through one or more conductors. Preferably, the sample application zone 106 is in direct contact with the first end 110 of the chromatographic medium 108.

The second opposable component 104 includes an applicator 120 and an absorber 122. The applicator 120 is for application of a wash liquid. When the first and second opposable components 102 and 104 are closed to bring them into opposition or operable contact, the applicator 120 is in operable contact with the sample application zone 106 and the absorber 122 is in operable contact with the second end 112 of the chromatographic medium 108. The second opposable component 104 also includes an aperture 124 for viewing of the detection zone 114 and, if present, the control zone 118 on the chromatographic medium 108. Alternatively, two apertures can be used, one for viewing of the detection zone 114 and another for viewing of the control zone 118.

The first and second opposable components 102 and 104 are joined by a hinge 126. The first and second opposable components 102 and 104 can include engagers such as locks 128 and 130 to hold the first and second opposable components 102 and 104 in opposition or in operable contact. Alternatively, the first and second opposable components 102 and 104 can be held in opposition or operable contact by means of an adhesive strip attached to one of the first or second opposable components 102 or 104. The adhesive strip can be provided with a releaseable liner. In another alternative, the first and second opposable components can be incorporated into a housing such as the housing of U.S. Pat. No. 5,441,698 to Norell or the housing of application Ser. No. 08/971,705 by Shields et al., both of which are incorporated in their entirety by this reference.

The device 100 can also include a sealing ridge or gasket 132. Preferably, the device also includes a barrier 134, such as a clear, self-adhesive film, to prevent fluid flow between the applicator 120 and the sample application zone 106 or the chromatographic medium 108 except as required for the application of the wash liquid by the applicator 120.

In the operation of this embodiment, first the sample, typically a whole blood sample, is applied to the sample application zone 106. Preferably, the whole blood sample is applied to the center of the sample application zone 106. Preferably, a measured volume of a running buffer is then applied to the lower portion of the sample application zone 106, i.e., the portion furthest away from the chromatographic medium 108, to displace the plasma from the sample application zone 106 and aid in resolubilizing the resolubilizable labeled second specific binding partner at the conjugate zone 116. The running buffer can be a buffer such as phosphate buffer, pH 7.5, or can be phosphate buffered saline. The sample then migrates into the chromatographic medium 108 and first reaches the conjugate zone 116. With the device 100 remaining open, a wash liquid, which can be the same running buffer that is applied to the sample application zone 106, is applied to the applicator 120. When the sample reaches the chromatographic medium 108, the device 100 is closed by bringing the first and second opposable components 102 and 104 into opposition or operable contact, causing the wash liquid to be applied to the sample application zone 106. This allows clearing of the background in the chromatographic medium 108 to increase the sensitivity of the assay performed by the device.

The wash liquid, also referred to as running buffer, is typically an aqueous liquid; it can be water, or can contain buffers or electrolytes. It can be, for example, sodium phosphate, phosphate-buffered saline, physiological saline, or another aqueous liquid. An example of a suitable wash liquid or running buffer is phosphate-buffered saline.

After the sample and resolubilized labeled specific binding partner have migrated through the chromatographic medium 108, including the detection zone 114 and the control zone 118, if present, the assay is read. A positive test is indicated by the presence of label at the detection zone 114 and at the control zone 118, if present. A negative test is indicated by the absence of label at the detection zone 114 and the presence of label at the control zone 118, if present. If the control zone 118 is present and label is not seen at the control zone 118 after the running of the test, the test is invalid and should be disregarded.

The test sample to be assayed in this device is typically whole blood. However, the device can also advantageously be used for assay of other body fluids that may contain or may be suspected of containing blood cells, such as urine, cerebrospinal fluid, or other biological fluids that may contain blood. Even though the blood may be itself an indicator of an abnormal condition, its presence can interfere with the assay of various analytes by immunoassays or other specific binding assays.

Various matrices of porous material permeable to the liquid portion of blood but capable of trapping the cellular components of blood are disclosed in U.S. patent application Ser. No. 08/437,850, filed May 9, 1995, and now abandoned, incorporated herein by this reference.

For example, the matrix can be a woven or non-woven fabric, paper, cellulose, glass fiber, polyester, other polymers, or mixtures of these materials to retain the cellular components of blood. In one alternative, the matrix has a binder for the cellular components of blood incorporated therein.

The binder for the cellular components of blood is typically a lectin or an anti-blood cell antibody. When the binder is an anti-blood cell antibody, it is typically an anti-erythrocyte antibody. Such antibodies are well known in the art and need not be described further here. Typically, they are obtained by the injection of red blood cells or fractions from red blood cells into a different species. If the desired antibody is anti-human red blood cell antibody, suitable animals for the production of such antibodies include goats, rabbits, horses, and sheep. Either polyclonal or monoclonal antibodies can be used. Alternatively, anti-leukocyte or anti-platelet antibodies can be used alone or in addition to the anti-red blood cell antibody if it is desired to ensure removal of those cellular components.

The binder for the cellular components of blood can be noncovalently bound to the matrix. Alternatively, it can be covalently cross-linked to the matrix; techniques for cross-linking proteins to solid supports such as cellulose, paper, and other typical sample pad materials are well-known in the art and need not be described further here. The matrix, containing antibodies or lectins, can be further treated with polyester binders to capture cellular elements, as described, for example, in U.S. Pat. No. 4,816,224 to Vogel et al., incorporated herein by reference. Other types of polymer binders can also be used.

When the binder is a lectin, typically the lectin is one of the following, but is not limited to: concanavalin A, abrin, phytohaemagglutinin, limulin, or one of the lectins produced by the following species: *Agaricus bisporus, Anguilla anguilla, Arachis hypogaea, Bandeiraea simplicifolia, Bauhinia purpurea, Caragana arborescens, Cicer arietinum, Codium fragile, Datura stramoniumn, Dolichos biflorus, Erythrina corallodendron, Erythrina cristagalli, Euonymnus europaeus, Glycine max, Helix aspersa, Helix pomatia, Lathyrus odoratus, Lens culinaris, Licopersicon esculentum, Maclura pomifera, Momordica charantia, Micoplasma gallisepticum, Naja mocambigue, Naja kaouthia, Perseun americana, Phaseolus coccineus, Phaseolus limesis, Phaseolus vulgaris, Phytolacca americana, Pisum sativum, Pseudomonas aeruginosa, Psophocarpus tetragonolobus, Ptilota plumosa, Ricinus communis, Robinia pseudoacacia, Sambucus nigra, Solanum tuberosum, Sophora japonica, Tetragonolobus purpureas, Triticum vulgaris, Ulex europaeus, Vicia faba, Vicia sativa, Vicia villosa, Vigna radiata, Viscum album,* and *Wisteria floribunda.* Lectins are proteins produced by plants and some animal species that bind specifically and non-covalently to sugar groups that are present on the surface of blood cells.

Preferably, the lectin is capable of binding both erythrocytes and leukocytes and is not blood-cell-group specific. Many other examples of lectins are known and need not be described further here.

The matrix can alternatively be impregnated with a carbohydrate capable of aggregating blood cells, such as the carbohydrates disclosed in U.S. Pat. No. 4,678,757 by Rapkin et al., incorporated herein by this reference. These carbohydrates include, but are not necessarily limited to, mannitol, sorbitol, inositol, $\beta$-D-glucose, $\alpha$-D-glucose, D(+) xylose, D(+)mannose, D(−)arabinose, L(+)arabinose, D(+) galactose, L(−)xylose, D-glucoheptose, L-lyxose, lactose, maltose, and sucrose. A particularly preferred carbohydrate is mannitol. Although applicants do not intend to be bound by this theory, these carbohydrates are believed to act by binding non-covalently to the surface of erythrocytes, making them adhesive and causing them to clump or aggregate.

A carbohydrate in solution is applied to a permeable matrix such as a non-woven fiber (e.g., cellulose, glass, or polyester) in a concentration up to 20% (w/v) to produce a treated matrix. The solution can be applied by various means such as impregnation, printing, or spraying to achieve the desired concentration in the matrix. The carbohydrate functions as a holding, clumping, or agglutinating agent which preferentially separates cells from the surrounding liquid which is free to migrate through the matrix.

In another alternative, the sample application zone can include an untreated asymmetric membrane. The untreated asymmetric membrane is constricted in such a way that it has a decreasing gradient of pore size within the membrane. The asymmetric membrane has a first surface and a second surface; the blood sample is applied to the first surface. The pore size decreases from the first surface to the second surface. The asymmetric membrane is capable of trapping the cellular components of blood within it and allowing the liquid components of blood to pass through.

Asymmetric membranes suitable for inclusion in a sample application zone of an assay device according to the present invention can be prepared from combinations of hydrophobic and hydrophilic polymers, such as disclosed in U.S. Pat. No. 5,240,862 to Koenhen et al. and U.S. Pat. No. 5,076,925 to Roesink et al. The hydrophobic polymer can be polysulfone, polyether sulfone, polyimide, or polyetherimide, and the hydrophilic polymer can be polyvinyl pyrrolidone, polyacrylic acid, polyvinyl alcohol, polyvinyl acetate, or polyethylene glycol.

In one preferred alternative, the matrix of porous material permeable to the liquid portion of blood but capable of trapping the cellular components of blood can include, for example, phosphate-buffered saline containing a detergent and a chelating agent.

The detergent can be a polyoxyethylene sorbitan monolaurate, a polyoxyethylene sorbitan monooleate, a polyoxyethylene sorbitan monopalmitate, a polyoxyethylene sorbitan monostearate, a polyoxyethylene sorbitan trioleate, a polyethylene glycol fatty alcohol ether, a polyoxyethylene fatty acid ester, or a polyoxyethylene ether. Preferably, the detergent is a polyoxyethylene ether such as Triton™ X-100 or a polyoxyethylene sorbitan monolaurate such as Tween™ 20. A preferred concentration of Tween™ 20 is about 0.1%.

The chelating agent can be EDTA or EGTA. Preferably, the chelating agent is EDTA. A preferred concentration of EDTA is about 0.15%.

Other methods for separating the cellular components of blood from the liquid portion of blood are known in the art and can be used in conjunction with the sample application zone 106.

C. Multiplex Devices

The foregoing description of an embodiment of the present invention is directed to a device that is constructed to perform one assay. However, the same principles can be used to construct multiplex devices that can perform more than one assay simultaneously on the same device.

The embodiment shown above in Section (B) can be used as the basis for a multiplex device, with the same specific binding partners. In multiplex devices according to the present invention, there is an equal number of elements located on the first opposable component and the second opposable component. Each set of elements functions exactly as do the corresponding elements in a single-assay device. The term "corresponding" is used herein to refer to the elements that come into contact when the first and second opposable components of the device are brought into opposition or operable contact in such a multiplex device.

Multiplex devices according to the present invention can have from 2 to as many as 15 or more separate chromatographic media for the performance of as many individual assays simultaneously as there are chromatographic media.

When multiple assays are performed simultaneously, the assays can be performed on the same analyte or different analytes. For example, the multiplex devices can be used to assay a number of different analytes and different aliquots of the same sample, or can be used to assay the same analyte in a number of different samples. This latter mode is particularly useful in assaying for conditions for which samples taken at different times from the same patient must be assayed for the analyte of interest. Alternatively, one or more of the assays can be used for controls or reference standards.

The labels of the labeled specific binding partners can be the same or different. Typically, the labels are the same. Typically, the label is a colloidal particle label, as described above. The colloidal particle label is preferably a colloidal carbon label.

Figure 2:
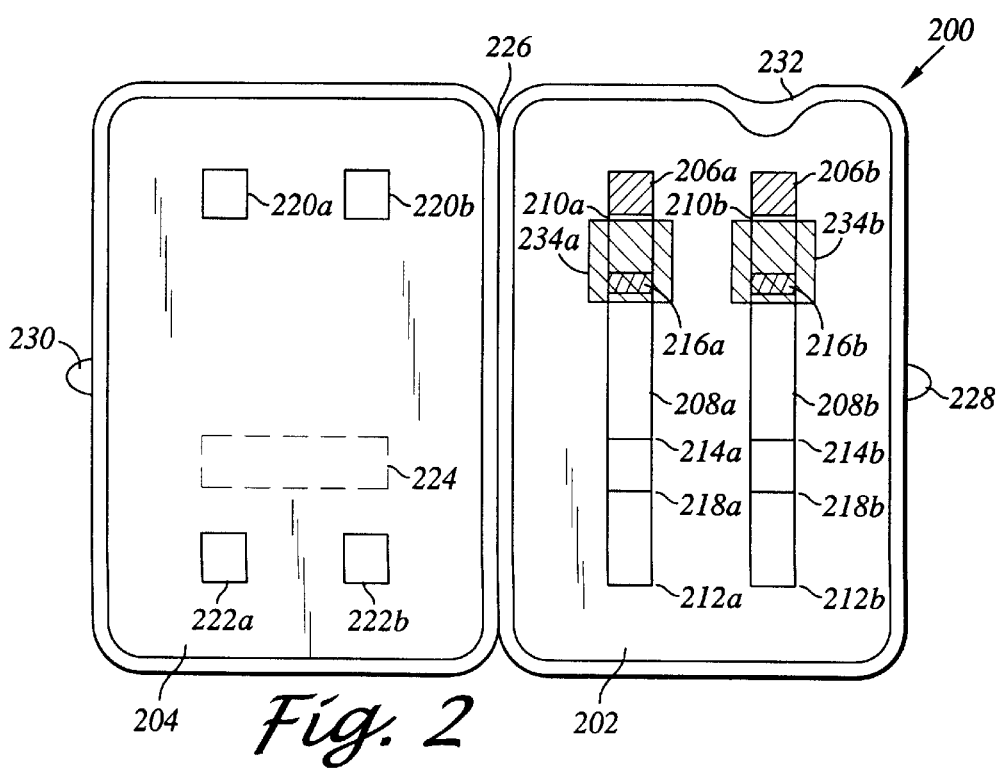
FIG. 2 is a drawing of an multiplex assay device according to the present invention particularly intended for use with a whole blood sample or samples and that can perform a number of assays simultaneously in the same assay device.

A multiplex assay device according to the present invention, with two chromatographic media for two simultaneous assays, is shown in FIG. 2. The device 200 includes a first opposable component 202 and a second opposable component 204. The first opposable component 202 has two sample application zones 206a and 206b that each contain a matrix of porous material permeable to the liquid portion of blood but capable of trapping the cellular components of blood. The first opposable component 202 also includes two chromatographic media 208a and 208b, each having first ends 210a and 210b and second ends 212a and 212b. The chromatographic media 208a and 208b each include detection zones 214a and 214b, conjugate zones 216a and 216b, and optionally control zones 218a and 218b. The conjugate zones 216a and 216b and control zones 218a and 218b are located on the chromatographic media 208a and 208b so that the conjugate zones 216a and 216b are located closer to the first ends 210a and 210b of the chromatographic media 208a and 208b than are the detection zones 214a and 214b. The control zones 218a and 218b, if present, are located furthest from the first ends 210a and 210b and closest to the second ends 212a and 212b of the chromatographic media 208a and 208b of the three zones.

The detection zones 214a and 214b each contain a first immobilized specific binding partner for the analyte. The conjugate zones 216a and 216b each contain a second labeled specific binding partner for the analyte in resolubilizable form. The control zones 218a and 218b can each contain a third specific binding partner specific for the second labeled specific binding partner but not binding the analyte bound by the corresponding first specific binding partner in the corresponding detection zones 214a and 214b. Alternatively, the control zones 218a and 218b can each contain immobilized analyte or analyte analogue. The labeled specific binding partners in the conjugate zones 216a and 216b and the unlabeled immobilized specific binding partners in the detection zones 214a and 214b can be the same or can be different for each chromatographic medium, depending on the analyte being assayed and the nature of the available specific binding partners.

The sample application zones 206a and 206b are each in operable contact with the first ends 210a and 210b of the chromatographic media 208a and 208b.

The second opposable component 204 includes applicators 220a and 220b and absorbers 222a and 222b. When the first and second opposable components 202 and 204 are closed to bring them into opposition or operable contact, the applicators 220a and 220b are in operable contact with the sample application zones 206a and 206b and the absorbers 222a and 222b are in operable contact with the second ends 212a and 212b of the chromatographic media 208a and 208b. The second opposable component 204 also includes an aperture 224 for viewing of the detection zones 214a and 214b and, if present, the control zones 218a and 218b on the chromatographic media 208a and 208b. Although FIG. 2 shows the device 200 with a single aperture 224, multiple apertures can alternatively be used for viewing of the detection zones 214a and 214b. The applicators 220a and 220b are for application of a wash liquid; the wash liquid can be the same or different for each applicator.

The first and second opposable components 202 and 204 are joined by a hinge 226. The first and second opposable components 202 and 204 can include engagers such as locks 228 and 230 to hold the first and second opposable components 202 and 204 in opposition or in operable contact. Alternatively, the first and second opposable components 202 and 204 can be held in opposition or operable contact by means of an adhesive strip attached to one of the first or second opposable components 202 or 204. The adhesive strip can be provided with a releaseable liner.

The device 200 can also include a sealing ridge or gasket 232. Preferably, the device also includes barriers 234a and 234b, such as clear, self-adhesive film, to prevent fluid flow between the applicators 220a and 220b and the sample application zones 206a and 206b or the chromatographic media 208a and 208b except as required for the application of the wash liquid by the applicators 220a and 220b.

The multiplex device 200 is used exactly as is the device shown in FIG. 1. At the commencement of the assay, a sample is added to one or more of the sample application zones 206a and 206b. At the conclusion of the assay, the detection zones 214a and 214b and the control zones 218a and 218b are viewed through the aperture 224 to detect or determine the presence of the analyte or analytes being tested for in the sample or samples.

D. Devices Including a Capture Zone and Validation Zone for the Assay of Analytes Using Murine Monoclonal Antibodies Another embodiment of an assay device according to the present invention is particularly adapted to perform assays using non-human monoclonal antibodies as the unlabeled immobilized specific binding partner and as the labeled mobile specific binding partner. Typically, the non-human monoclonal antibodies are murine monoclonal antibodies. This embodiment employs a capture zone to capture human anti-non-human antibodies that might otherwise interfere with the assay by reacting with the monoclonal antibodies that are used in the assay, as well as a validation zone that gives a direct indication of the existence of interference that might be caused by the presence of such human antibodies in the sample to be assayed.

Figure 3:
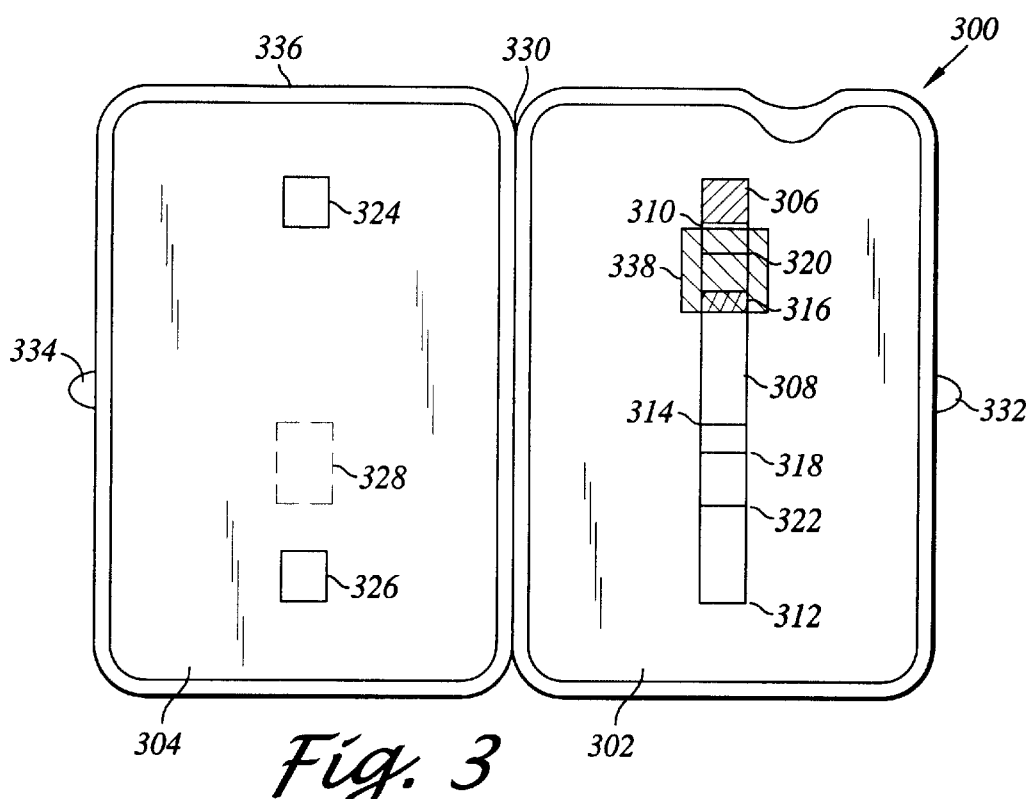
FIG. 3 is a drawing of a first version of an embodiment of an assay device according to the present invention employing a capture zone and a validation zone on the chromatographic medium.

One version of this embodiment, employing a capture zone and a validation zone on the chromatographic medium, is shown in FIG. 3. In this version of the embodiment, the specific binding partners are as follows: (1) a first specific binding partner binding an analyte, the first specific binding partner being immobilized in a detection zone on the chromatographic medium; (2) a second specific binding partner binding the analyte, the second specific binding partner being located in a conjugate zone in resolubilizable form on the chromatographic medium; (3) a third specific binding partner binding human antibodies that bind the first or second specific binding partners, the third specific binding partner being located in a capture zone on the chromatographic medium; (4) a fourth specific binding partner binding human antibodies that bind the first or second specific binding partners, the fourth specific binding partner being immobilized in a validation zone on the chromatographic medium; and (5) optionally, a fifth specific binding partner immobilized at a control zone on the chromatographic medium, the fifth specific binding partner specifically binding the second specific binding partner but not binding the analyte. The fifth specific binding partner at the control zone can be replaced by an analyte or analyte analogue.

The assay device 300 comprises a first opposable component 302 and a second opposable component 304. The first opposable component 302 includes a sample application zone 306 that contains a matrix of porous material permeable to the liquid portion of blood but capable of trapping the cellular components of blood, as described above. The first opposable component 302 also includes a chromatographic medium 308 having a first end 310 and a second end 312. The chromatographic medium 308 includes a detection zone 314, a conjugate zone 316, optionally, a control zone 318, and a capture zone 320 and a validation zone 322. These zones are typically located on the chromatographic medium 308 so that the capture zone 320 is located closest to the first end 310 of the chromatographic medium 308. The conjugate zone 316 is located next closest to the first end 310 of the chromatographic medium 308, but further from the first end 310 than the capture zone 320. The detection zone 314 typically is located next closest to the first end 310 of the chromatographic medium 308, but further from the first end 310 than the conjugate zone 316. The detection zone 314 is located far enough from the capture zone 320 that antibodies captured and held in the capture zone 320 do not "bleed over" into the detection zone 314. The control zone 318 and the validation zone 322 can be located closer than the detection zone 314 to the second end 312 of the chromatographic medium 308 in either order.

The detection zone 314 contains a first immobilized specific binding partner for the analyte, as described above. The conjugate zone 316 contains a second labeled specific binding partner for the analyte, as described above. The control zone 318 contains a fifth specific binding partner specific for the second labeled specific binding partner but that does not bind the analyte. Alternatively, the control zone 318 can contain immobilized analyte or analyte analogue, as described above.

In this alternative, the capture zone 320 contains a third specific binding partner. The third specific binding partner can either be immobilized or mobile. The validation zone 322 contains a fourth specific binding partner. The fourth specific binding partner is an immobilized specific binding partner that is specific for human antibodies that bind to the non-human monoclonal antibody. In this alternative, the presence of detectable label at the validation zone 322 indicates interference in the assay caused by the presence of human-anti-mouse antibodies (HAMA). The detectable label is the second specific binding partner, which is a mobile labeled specific binding partner for the analyte as described above.

Typically, in this alternative, the third and fourth specific binding partners are mouse immunoglobulin G or a derivative or polymer of mouse immunoglobulin G. For example, although not by way of limitation, the third specific binding partner at the capture zone 320 can be mouse serum as a source of mouse IgG, and the fourth specific binding partner at the validation zone 322 can be a murine monoclonal antibody against α-fetoprotein (AFP). A particularly suitable monoclonal antibody against AFP is an anti-AFP antibody produced by Hybritech (San Diego, Calif.) and designated AFU 212.7. This monoclonal antibody can be replaced by any other murine monoclonal antibody that does not bind to either the analyte or the second specific binding partner.

As another alternative, when the device detects hCG, the capture zone 320 can contain, in a suitable buffer, such as phosphate buffered saline, pH 7.4, 2% bovine serum albumin, and 4% Triton X-100, 0.6 mg/ml Poly MAK33, a heterophilic scavenger antibody (Boehringer Mannheim), 12 μg/ml of monoclonal anti-LH antibody (Uybritech 12119, San Diego, Calif.), and 1 mg/ml of bovine IgG. In this alternative, the third specific binding partner is the Poly MAK33. Poly MAK33 is a mAb IgG1/F(ab') polymer that efficiently scavenges human anti-mouse antibodies, particularly those specific for IgG1 mouse IgG. The anti-LH antibody is to scavenge luteinizing hormone, which may cross-react with hCG. When the device is to detect one of the related glycoprotein hormones other than hCG, such as LH, TSH, or FSH, the anti-LH antibody is replaced by one or more of anti-CG antibody, anti-LH antibody, anti-TSH antibody or anti-FSH antibody, depending on the analyte to be detected, in order to minimize cross-reactions. Antibodies specific for the analyte to be detected are not included at the capture zone 320.

The third specific binding partner serves to scavenge any human anti-mouse immunoglobutin G present in the sample. Only if the level of human anti-mouse immunoglobulin G antibodies is so high that the third specific binding partner at the capture zone 320 cannot scavenge the antibodies does detectable label appear at the validation zone 322 bound to the fourth specific binding partner, thus indicating the presence of interference, such as potential false negative or false positive results, due to HAMA.

Although non-human monoclonal antibodies are used for the first and second specific binding partners in this alternative, the present invention is not limited to the use of non-human monoclonal antibodies for the first and second specific binding partners. Other types of monoclonal antibodies, such as humanized or partially humanized monoclonal antibodies, can be used for these specific binding partners. In a less preferred alternative, it can also be possible to use highly affinity purified polyclonal antibodies for these specific binding partners.

The sample application zone 306 of the device 300 is in operable contact with the first end 310 of the chromatographic medium 308. The operable contact between the first end 310 of the chromatographic medium 308 and the sample application zone 306 can be direct contact or can be contact through one or more conductors. Preferably, the sample application zone 306 is in direct contact with the first end 310 of the chromatographic medium 308.

The second opposable component 304 includes an applicator 324 and an absorber 326. The applicator 324 is for application of a wash liquid. When the first and second opposable components 302 and 304 are closed to bring them into opposition or operable contact, the applicator 324 is in operable contact with the sample application zone 306 and the absorber 326 is in operable contact with the second end 312 of the chromatographic medium 308. The second opposable component 304 also includes an aperture 328 for viewing of the detection zone 314, the control zone 318, and the validation zone 322. The aperture 328 can have markings indicating the position of the detection zone 314, the control zone 318 and the validation zone 322 for the user. Alternatively, there can be separate apertures for the viewing of the detection zone 314, the control zone 318, and the validation zone 322, marked as appropriate.

The first and second opposable components 302 and 304 are joined by a hinge 330. The first and second opposable components 302 and 304 can include engagers such as locks 332 and 334 to hold the first and second opposable components 302 and 304 in opposition or in operable contact. Alternatively, the first and second opposable components 302 and 304 can be held in opposition or operable contact by means of adhesive strip attached to one of the first or second opposable components 302 or 304. The adhesive strip can be provided with a releaseable liner.

The device can also include a sealing ridge or gasket 336. Preferably, the device also includes a barrier 338, such as a clear, self-adhesive film, to prevent fluid flow between the applicator 324 and the sample application zone 306 or the chromatographic medium 308 except as required for the application of the wash liquid by the applicator 324.

In the operation of this version of this embodiment, first the sample, typically a whole blood sample, is applied to the sample application zone 306 as described above. Preferably, the whole blood sample is applied to the center of the sample application zone 306. Preferably, a measured volume of a running buffer as described above is then applied to the lower portion of the sample application zone 306, i.e., the portion furthest away from the chromatographic medium 308, to displace the plasma from the sample application zone 306 and aid in resolubilizing the resolubilizable labeled second specific binding partner at the conjugate zone 316. The sample then migrates into the chromatographic medium 308 and first reaches the capture zone 318. At the capture zone 318, human antibodies that would bind the first and second specific binding partners are captured and retained. The sample then reaches the conjugate zone 316, where the labeled second specific binding partner for the analyte is resolubilized. With the device 300 remaining open, a wash liquid as described above is applied to the applicator 324. When the sample reaches the chromatographic medium, the device 300 is closed by bringing the first and second opposable components 302 and 304 into opposition or operable contact, causing the wash liquid to be applied to the sample application zone 306. This allows clearing of the background in the chromatography medium 308 to increase the sensitivity of the assay performed by the device.

After the sample and the resolubilized labeled specific binding partner have migrated through the chromatographic medium 308, including the detection zone 314, the control zone 318 and the validation zone 320, the assay is read. A positive test is indicated by the presence of label at the detection zone 314 and the control zone 318, and by the absence of label at the validation zone 320. A negative test is indicated by the absence of label at the detection zone 314 and at the validation zone 320, and by the presence of label at the control zone 318. If label is absent at the control zone 318 or is present at the validation zone 320, the test is invalid and should be disregarded.

In another version of this embodiment, the capture zone is located within the sample application zone and there is no separate capture zone.

The specific binding partners employed in this embodiment are as follows: (1) a first specific binding partner located in the sample application zone; (2) a second specific binding partner binding an analyte, the second specific binding partner being immobilized in a detection zone on the chromatographic medium; (3) a third specific binding partner binding the analyte, the third specific binding partner being located in a conjugate zone in resolubilizable form on the chromatographic medium; (4) a fourth specific binding partner binding human antibodies that bind the first or second specific binding partners, the fourth specific binding partner being located in a validation zone on the chromatographic medium; and (5) optionally, a fifth specific binding partner immobilized at a control zone on the chromatographic medium, the fifth specific binding partner specifically binding the second specific binding partner but not binding the analyte. The fifth specific binding partner at the control zone can be replaced by an analyte or analyte analogue. The first specific binding partner located at the sample application zone binds human antibodies that bind the second or third specific binding partners.

Figure 4:
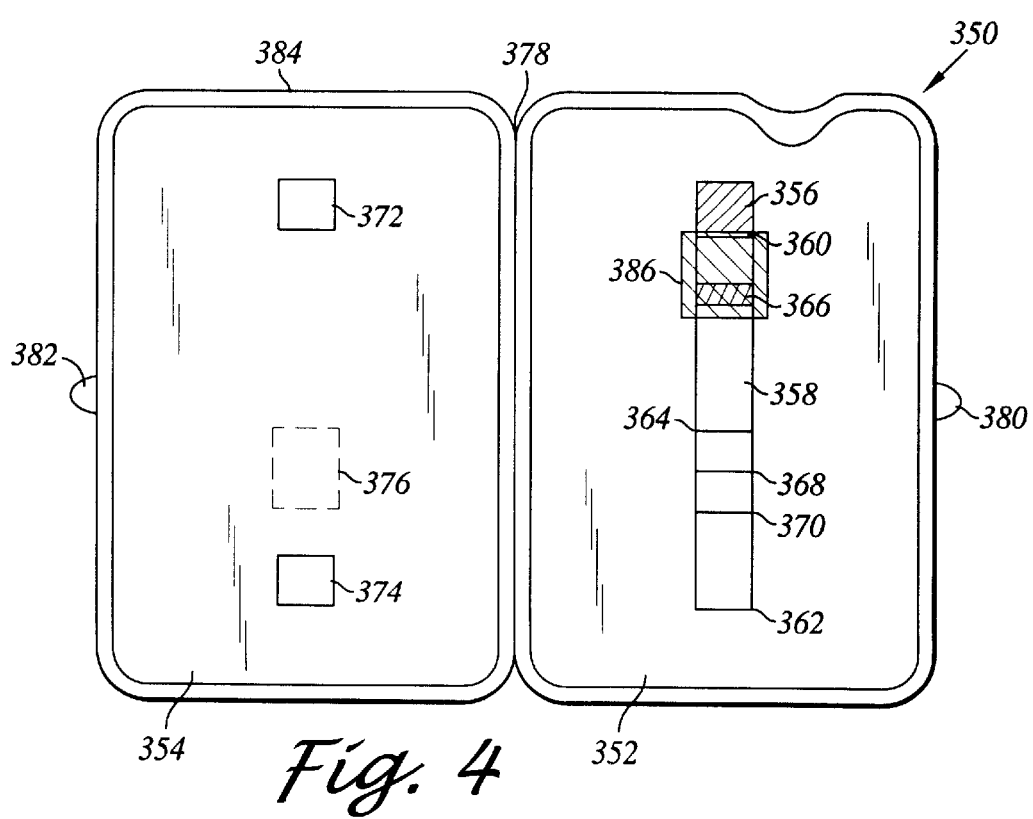
FIG. 4 is a drawing of a second version of an embodiment of an assay device according to the present invention employing a validation zone on the chromatographic medium and a specific binding partner located at the sample application zone.

This version of the embodiment is shown in FIG. 4. The device 350 includes a first opposable component 352 and a second opposable component 354. The first opposable component 352 includes a sample application zone 356 that contains a matrix of porous material permeable to the liquid portion of blood but capable of trapping the cellular components of blood, as described above. The sample application zone 356 also includes the first specific binding partner, as described above. The first opposable component 302 also includes a chromatographic medium 358 having a first end 360 and a second end 362. The chromatographic medium 358 includes a detection zone 364, a conjugate zone 366, optionally, a control zone 368, and a validation zone 370. These zones are typically located on the chromatographic medium 358 so that the conjugate zone 366 is located closest to the first end 360 of the chromatographic medium 358. The detection zone 364 typically is located next closest to the first end 360 of the chromatographic medium 358, but further from the first end 360 than the conjugate zone 366. The detection zone 364 is located far enough from the sample application zone 356 that antibodies captured and held in the sample application zone 356 do not "bleed over" into the detection zone 364. The control zone 368 and the validation zone 370 can be located closer than the detection zone 364 to the second end 362 of the chromatographic medium 358 in either order.

The detection zone 364 contains the second specific binding partner, which is an immobilized specific binding partner for the analyte, as described above. The conjugate zone 366 contains the third specific binding partner, which is a labeled specific binding partner for the analyte, as described above. The control zone 368, if present, contains a fifth specific binding partner that is specific for the second labeled specific binding partner but that does not bind the analyte. Alternatively, the control zone 368 can contain immobilized analyte or analyte analogue, as described above.

In this alternative, the sample application zone 356 contains a first specific binding partner, as described above. The validation zone 370 contains a fourth specific binding partner, as described above.

The first specific binding partner at the sample application zone 356 serves to scavenge any human anti-mouse immunoglobulin G present in the sample. Only if the level of human anti-mouse immunoglobulin G antibodies is so high that the first specific binding partner at the sample application zone 356 cannot scavenge the antibodies does detectable label appear at the validation zone 370, thus indicating the presence of interference, such as potential false negative or false positive results, due to HAMA, as discussed above.

Although non-human monoclonal antibodies are used for the second and third specific binding partners in this alternative, the present invention is not limited to the use of non-human monoclonal antibodies for the second and third specific binding partners, as discussed above.

The sample application zone 356 of the device 350 is in operable contact with the first end 360 of the chromatographic medium 358. The operable contact between the first end 360 of the chromatographic medium 358 and the sample application zone 356 can be direct contact or can be contact through one or more conductors.

The second opposable component 354 includes an applicator 372 and an absorber 374. The applicator 372 is for application of a wash liquid. When the first and second opposable components 352 and 354 are closed to bring them into opposition or operable contact, the applicator 372 is in operable contact with the sample application zone 356 and the absorber 374 is in operable contact with the second end 362 of the chromatographic medium 358. The second opposable component 354 also includes an aperture 376 for viewing of the detection zone 364, the control zone 368, and the validation zone 370. The aperture 376 can have markings indicating the position of the detection zone 364, the control zone 368 and the validation zone 370 for the user, as described above. Alternatively, there can be separate apertures for the viewing of the detection zone 364, the control zone 368, and the validation zone 370, marked as appropriate.

The first and second opposable components 352 and 354 are joined by a hinge 378. The first and second opposable components 352 and 354 can include engagers such as locks 380 and 382 to hold the first and second opposable components 352 and 354 in opposition or in operable contact. Alternatively, the first and second opposable components 352 and 354 can be held in opposition or operable contact by means of an adhesive strip attached to one of the first or second opposable components 352 or 354. The adhesive strip can be provided with a releaseable liner.

The device can also include a sealing ridge or gasket 384. Preferably, the device also includes a barrier 386, such as a clear, self-adhesive film, to prevent fluid flow between the applicator 372 and the sample application zone 356 or the chromatographic medium 358 except as required for the application of the wash liquid by the applicator 372.

In the operation of this version of this embodiment, first the sample, typically a whole blood sample, is applied to the sample application zone 356 as described above. Preferably, the whole blood sample is applied to the center of the sample application zone 356. In the operation of this version of the embodiment, the sample is allowed to remain at the sample application zone 356 for a sufficient time to enable the first specific binding partner to bind any human anti-non-human antibody present in the sample so that human antibodies that would bind the second and third specific binding partners are captured and retained. Preferably, a measured volume of a running buffer as described above is then applied to the lower portion of the sample application zone 356, i.e., the portion furthest away from the chromatographic medium 358, to displace the plasma from the sample application zone 356 and aid in resolubilizing the resolubilizable labeled third specific binding partner at the conjugate zone 366. The sample then migrates into the chromatographic medium 358. The sample then reaches the conjugate zone 366, where the labeled third specific binding partner for the analyte is resolubilized. With the device 350 remaining open, a wash liquid as described above is applied to the applicator 372. When the sample reaches the chromatographic medium, the device 350 is closed by bringing the first and second opposable components 352 and 354 into opposition or operable contact, causing the wash liquid to be applied to the sample application zone 356. This allows clearing of the background in the chromatographic medium 358 to increase the sensitivity of the assay performed by the device.

After the sample and the resolubilized labeled specific binding partner have migrated through the chromatographic medium 358, including the detection zone 364, the control zone 368 and the validation zone 370, the assay is read. A positive test is indicated by the presence of label at the detection zone 364 and the control zone 368, and by the absence of label at the validation zone 370. A negative test is indicated by the absence of label at the detection zone 364 and at the validation zone 370, and by the presence of label at the control zone 368. If label is absent at the control zone 368 or is present at the validation zone 370, the test is invalid and should be disregarded.

Figure 5:
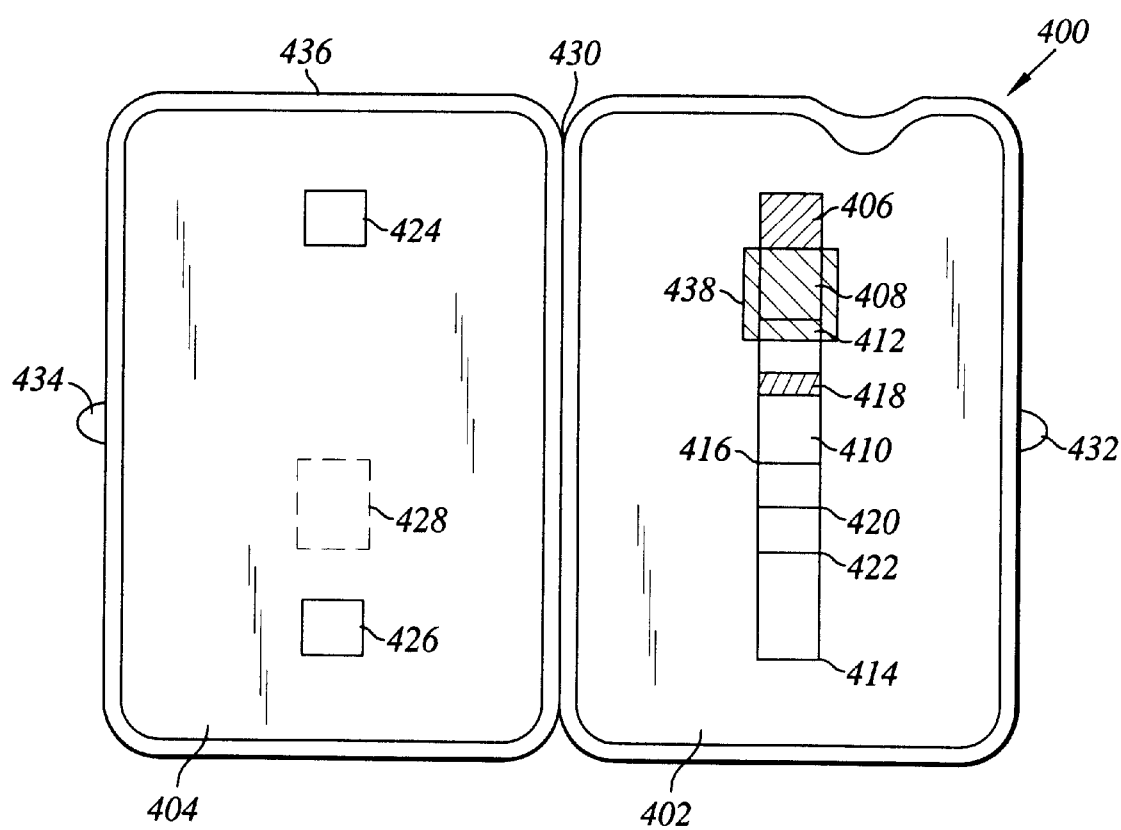
FIG. 5 is a drawing of a third version of an embodiment of an assay device according to the present invention employing a validation zone on the chromatographic medium and a capture zone located in a conductor.

In a third version of this embodiment, the capture zone is located within a conductor that bridges the sample application zone and the first end of the chromatographic medium. This third version of this embodiment is shown in FIG. 5.

The specific binding partners in this third version of the embodiment are as follows: (1) a first specific binding partner located within a conductor that bridges the sample application zone and the first end of the chromatographic medium; (2) a second specific binding partner binding an analyte, the second specific binding partner being immobilized in a detection zone on the chromatographic medium; (3) a third specific binding partner binding the analyte, the third specific binding partner being located in a conjugate zone in resolubilizable form on the chromatographic medium; (4) a fourth specific binding partner binding human antibodies that bind the first or second specific binding partners, the fourth specific binding partner being located in a validation zone on the chromatographic medium; and (5) optionally, a fifth specific binding partner immobilized at a control zone on the chromatographic medium, the fifth specific binding partner specifically binding the second specific binding partner but not binding the analyte. The fifth specific binding partner at the control zone can be replaced by an analyte or analyte analogue. The first specific binding partner located at the conductor binds human antibodies that bind the second or third specific binding partners.

The device 400 includes a first opposable component 402 and a second opposable component 404. The first opposable component 402 includes a sample application zone 406 that contains a matrix of porous material permeable to the liquid portion of blood but capable of trapping the cellular components of blood, as described above. The first opposable component 402 also includes a conductor 408 that is in operable contact with the sample application zone 406. The conductor includes the first specific binding partner, as described above. The first opposable component 302 also includes a chromatographic medium 410 having a first end 412 and a second end 414. The first end 412 of the chromatographic medium 410 is in operable contact with the conductor 408 so that the conductor 408 bridges the sample application zone 406 and the chromatographic medium 410. The chromatographic medium 410 includes a detection zone 416, a conjugate zone 418, optionally, a control zone 420, and a validation zone 422. These zones are typically located on the chromatographic medium 410 so that the conjugate zone 418 is located closest to the first end 412 of the chromatographic medium 410. The detection zone 416 typically is located next closest to the first end 412 of the chromatographic medium 410, but further from the first end 412 than the conjugate zone 418. The detection zone 416 is located far enough from the conductor 408 that antibodies captured and held in the conductor 408 do not "bleed over"into the detection zone 416. The control zone 420 and the validation zone 422 can be located closer than the detection zone 416 to the second end 414 of the chromatographic medium 410 in either order.

The detection zone 416 contains a second specific binding partner, which is an immobilized specific binding partner for the analyte, as described above. The conjugate zone 418 contains a third specific binding partner, which is a labeled specific binding partner for the analyte, as described above. The control zone 420 contains a fifth specific binding partner, which is a specific binding partner specific for the second labeled specific binding partner but that does not bind the analyte. Alternatively, the control zone 420 can contain immobilized analyte or analyte analogue, as described above.

In this alternative, the conductor 408 contains a first specific binding partner, as described above. The validation zone 422 contains a fourth specific binding partner, as described above.

The first specific binding partner serves to scavenge any human anti-mouse immunoglobulin G present in the sample. Only if the level of human anti-mouse immunoglobulin G antibodies is so high that the first specific binding partner at the conductor 408 cannot scavenge the antibodies does detectable label appear at the validation zone 422, thus indicating the presence of interference, such as potential false negative or false positive results, due to HAMA, as discussed above.

Although non-human monoclonal antibodies are typically used for the second and third specific binding partners in this alternative, the present invention is not limited to the use of non-human monoclonal antibodies for the second and third specific binding partners, as discussed above.

The second opposable component 404 includes an applicator 424 and an absorber 426. The applicator 424 is for application of a wash liquid, as discussed above. When the first and second opposable components 402 and 404 are closed to bring them into opposition or operable contact, the applicator 424 is in operable contact with the sample application zone 406 and the absorber 426 is in operable contact with the second end 414 of the chromatographic medium 410. The second opposable component 404 also includes an aperture 428 for viewing of the detection zone 416, the control zone 420, and the validation zone 422. The aperture 428 can have markings indicating the position of the detection zone 416, the control zone 420 and the validation zone 422 for the user, as described above. Alternatively, there can be separate apertures for the viewing of the detection zone 416, the control zone 420, and the validation zone 422, marked as appropriate.

The first and second opposable components 402 and 404 are joined by a hinge 430. The first and second opposable components 402 and 404 can include engagers such as locks 432 and 434 to hold the first and second opposable components 402 and 404 in opposition or in operable contact. Alternatively, the first and second opposable components 402 and 404 can be held in opposition or operable contact by means of an adhesive strip attached to one of the first or second opposable components 402 or 404. The adhesive strip can be provided with a releaseable liner.

The device can also include a sealing ridge or gasket 436. Preferably, the device also includes a barrier 438, such as a clear, self-adhesive film, to prevent fluid flow between the applicator 424 and the sample application zone 406.

In the operation of this version of this embodiment, first the sample, typically a whole blood sample, is applied to the sample application zone 406 as described above. Preferably, the whole blood sample is applied to the center of the sample application zone 406. Preferably, a measured volume of a running buffer as described above is then applied to the lower portion of the sample application zone 406, i.e., the portion furthest away from the chromatographic medium 410, to displace the plasma from the sample application zone 406 and aid in resolubilizing the resolubilizable labeled third specific binding partner at the conjugate zone 418. The sample then migrates through the conductor 408 and into the chromatographic medium 410. In the conductor 408, human antibodies that would bind the second and third specific binding partners are captured and retained. The sample then reaches the conjugate zone 418, where the labeled third specific binding partner for the analyte is resolubilized. With the device 400 remaining open, a wash liquid as described above is applied to the applicator 424. When the sample reaches the chromatographic medium, the device 400 is closed by bringing the first and second opposable components 402 and 404 into opposition or operable contact, causing the wash liquid to be applied to the sample application zone 406. This allows clearing of the background in the chromatographic medium 410 to increase the sensitivity of the assay performed by the device.

After the sample and the resolubilized labeled specific binding partner have migrated through the chromatographic medium 410, including the detection zone 416, the control zone 420 and the validation zone 422, the assay is read. A positive test is indicated by the presence of label at the detection zone 416 and the control zone 420, and by the absence of label at the validation zone 422. A negative test is indicated by the absence of label at the detection zone 416 and at the validation zone 422, and by the presence of label at the control zone 420. If label is absent at the control zone 420 or is present at the validation zone 422, the test is invalid and should be disregarded.

II. ANALYTES AND SPECIFIC BINDING PARTNERS FOR USE WITH ASSAY DEVICES

The analytes suitable for detection with an assay device according to the present invention include antigens, haptens, and antibodies. Antigens detectable with the device include bacterial antigens, protozoan antigens, viral antigens, cell-surface receptor proteins, enzymes, antibodies, hemoglobin, and hormones. Particular examples of bacterial antigens are antigens such as Streptococcus A and B antigens. Protozoan antigens include antigens specific for the protozoan parasite Giardia. Viral antigens include antigens specific for HIV and the Australia antigen specific for hepatitis.

One significant category of antigens detectable with the device is protein, polypeptide, and glycoprotein hormones. Such hormones include, but are not limited to, human chorionic gonadotropin (hCG), luteinizing hormone (LH), follicle stimulating hormone (FSH), thyroid stimulating hormone (TSH), corticotropin-releasing hormone (CRH), growth-hormone releasing hormone (GHRH), prolactin, human growth hormone (hGH), βlipotropin, corticotropin, βendorphin, calcitonin, parathormone, human placental lactogen (hPL), insulin, glucagon, pancreatic polypeptide (PP), secretin, cholecystokinin-pancreozymin, motilin, vasoactive intestinal peptide, gastric inhibitory peptide, and erythropoietin.

Antigens particularly suited to detection by assay devices according to the present invention include hCG, LH, FSH, and TSH.

Antibodies that can be detected include antibodies to bacteria such as *Helicobacter pylori* and to viruses including HIV.

Haptens that can be assayed include haptens to which antibodies of sufficient specificity can be prepared.

One antigen for which devices according to the present invention are particularly suitable is hCG. The detection of hCG is used widely as a test for pregnancy. Clearly, high accuracy and high sensitivity are important in the assay of hCG because the diagnosis of pregnancy or its absence has many social, psychological, and medical consequences and it is crucial that such diagnosis be available as early as possible in a pregnancy and be highly accurate. Other antigens for which devices according to the present invention are particularly suitable are the closely related glycoprotein hormones TSH, FSH, and LH.

If the analyte is an antigen or a hapten and a sandwich procedure is used, the first and second specific binding partners are preferably antibodies. In many applications, it is preferable if the first and second specific binding partners are antibodies to different epitopes on the analyte, but this is not necessarily required in the case of an antigen that has multiple copies of the same epitope, such as a viral capsid made up of repetitive protein subunits or a multi-subunit protein that contains multiple copies of the same polypeptide chain.

The antibodies can be polyclonal or monoclonal and can be IgG, IgM, or IgG. In most applications, IgG antibodies are preferred. In some applications, polyclonal antibodies are preferred, as their natural variability may allow more detection in systems where antigenic polymorphisms exist or may exist. However, where extreme sensitivity and freedom from cross-reactivity is required, monoclonal antibodies are particularly suited for use with assay devices according to the present invention. Monoclonal antibodies are particularly suited for the detection of protein and glycoprotein hormones such as hCG, FSH, LH, and TSH.

One particular analyte for which monoclonal antibodies are particularly suited is hCG. This is because of the need to avoid cross-reactivity between hCG and luteinizing hormone (LH). Therefore, a monoclonal antibody that is specific for the βsubunit of hCG and lacks cross-reactivity with LH is preferably used as a labeled second specific binding for assay of hCG. In this assay, a monoclonal antibody that is specific for the α-subunit of hCG is preferably used as the first specific binding partner, the specific binding partner immobilized on the chromatographic medium at the detection zone. This is an example of a two-antibody sandwich immunoassay employing monoclonal antibodies, an assay format described in U.S. Pat. No. 4,376,110 to David et al. and in U.S. Pat. No. 4,486,530 to David et al., both incorporated herein by this reference.

Where the analyte is a hapten and a sandwich immunoassay procedure is used, it is strongly preferred that the first and second specific binding partners be antibodies of different epitopes; otherwise, there may be an undesirable competition reaction set up that may interfere with binding of a complex of the labeled specific binding partner and the analyte to the immobilized second specific binding partner. It is recognized that not all haptens are large enough to accommodate more than one epitope; however, some haptens that are not large enough to induce antibody formation efficiently when injected by themselves are nevertheless large enough that they possess more than one epitope. In cases where antibodies to more than one epitope for a hapten cannot be obtained, competitive immunoassay procedures are generally preferred.

When the analyte is an antibody, and a sandwich immunoassay procedure is used, the labeled specific binding partner is typically a labeled antibody that binds to the analyte on the basis of species, class, or subclass (isotype) specificity. It is highly preferred that the labeled specific binding partner to an antibody analyte binds to the constant region of the antibody analyte, in order to prevent interference. When the analyte is an antibody, the unlabeled, immobilized specific binding partner is preferably an antigen, a hapten, or an antigen or hapten analog for which the antibody analyte is specific.

In some applications, it is desirable to employ indirect labeling. For example, in testing for Giardia antigen, an IgM antibody can be used that may be difficult to label directly. In that case, a secondary specific binding partner specific for a mobile second specific binding partner can be labeled. Typically, the labeled secondary specific binding partner binds to the antibody that is mobile on the basis of species, class, or subclass specificity. As an alternative to the use of a secondary specific binding partner, a mobile specific binding partner can be conjugated to biotin and an avidin-conjugated or streptavidin-conjugated label can be used.

As indicated above, the chromatographic medium has a detection zone that contains an immobilized specific binding partner for the analyte. The immobilized specific binding partner can be bound to the chromatographic medium by either covalent or noncovalent means; covalent means are generally preferred. Methods for immobilizing specific binding partners, particularly antibodies, on a chromatographic medium such as nitrocellulose or other solid phases are well known in the art and need not be described further here. Such methods are described, for example, in P. Tijssen, "Practice and Theory of Enzyme Immunoassays" (Elsevier, Amsterdam, 1985), ch. 13, pp. 297–328.

Similar methods can be used to immobilize an appropriate specific binding partner at the capture zone or at the sample preparation zone, as appropriate, and at the validation zone, for those embodiments employing capture and validation zones.

III. TEST KITS

Another aspect of the present invention is test kits.

A test kit according to the present invention comprises, in separate containers:

(1) a chromatographic assay device according to the present invention;

(2) a wash liquid to be applied to the appropriate applicator or applicators, in the case of a multiplex device, on the second opposable component; and, optionally (3) any additional reagent for treating or extracting a sample.

Components required in (2) and (3) are packaged separately and can be in liquid or solid form (freeze-dried, crystallized, precipitated, or aggregated). If the latter, they are resolubilized by the user, typically with distilled or purified water, with physiological saline, or with a buffer solution. As stated above, for a test kit incorporating a multiplex assay device, more than one wash liquid can be used and included in the test kit, separately packaged.

In test kits incorporating embodiments of the present inventions in which the wash liquid applied to the applicator and the running buffer applied to the sample application zone are different, the kits include both the wash liquid applied to the applicator and the running buffer applied to the sample application zone. However, typically, the wash liquid applied to the application and the running buffer applied to the sample application zone is the same, and is included in the kit.

ADVANTAGES OF THE PRESENT INVENTION

The present invention provides assay devices that perform improved unidirectional immunochromatographic assays for analytes in blood samples. The use of the unidirectional assay format improves sensitivity, because the assay format is not "capture limited," as a bidirectional format would be. The present invention allows the use of a unidirectional format while at the same time providing freedom from interference that would otherwise be caused by the colored background of a blood sample. This provides increased sensitivity and accuracy of the assay.

Chromatographic assay devices according to the present invention provide an advantage in being constricted of opposable elements. These use of opposable elements provides great versatility, as it permits the performance of reactions in a number of different sequences. This is possible because the use of such opposable elements allows the delivery of reagents to precisely defined regions of a chromatographic medium or other reaction component.

The use of opposable elements also provides optimum performance with minimum consumption of reagents by ensuring that reagents are not wasted by being sequestered in dead volumes of apparatus. The use of opposable components also provides optimum containment of possibly contaminated blood samples, such as those containing HIV or hepatitis virus.

Another advantage of assay devices according to the present invention lies in the ability of the devices to use pressure to drive fluids from one opposable component to the other and through the chromatographic medium and the control of pressure applied so that the pressure is optimum for each assay to be carried out. This accelerates the assay process and allows the performance of operations such as extraction within the assay device. It also reduces the dead volume of reagents remaining in components, allowing the use of smaller samples and smaller quantities of expensive or hard-to-purify reagents such as labeled antibodies.

Additionally, chromatographic assay devices according to the present invention allow the rapid and accurate detection of clinically important analytes, particularly hCG, assayed as a pregnancy test.

The use of colloidal carbon labels in a resolubilizable form provide extremely rapid kinetics of labeling. This aids in the separation of contaminants and improves the performance of the assay.

Additionally, particularly when used with a whole blood sample, the construction and arrangement of the housing of the device aids in the performance of the assay by assuring the withdrawal of excess immunoglobulin-containing samples which could otherwise create interference.

Another advantage of assay devices according to the present invention is the use of a conjugate zone that is dried down directly on the chromatographic medium allowing resolubilization without the use of a conjugate pad or other separate element.

Extraction of biological samples such as blood, sputum, or feces can be performed directly in the device, reducing the quantity of contaminated material that must be disposed and reducing the likelihood of accidental infection of physicians, technicians, or the public by such contaminated material.

Test methods using the devices according to the present invention have a wide dynamic range particularly suitable for the assay of analytes in whole blood samples, increasing the quantity of sample reaching the detection zone by the use of a unidirectional assay and therefore increasing the sensitivity of the assay. Additionally, the present invention allows for any desired length of preincubation of the reactants, and provides more homogeneous mixing of the analyte and labeled specific binding partner.

Although the present invention has been described in considerable detail, with reference to certain preferred versions thereof, other versions and embodiments are possible. These versions include other arrangements of two-assay devices that operate by the basic principles described herein.

In particular, devices according to the present invention can be adapted to make use of radial or circumferential flow through a chromatographic medium instead of linear flow. The present invention further encompasses variations in which the two components of the device are not held in a permanently fixed arrangement, but can be separated and brought together to perform the assay, such as by electrical or magnetic forces or by using a separable fastener such as a hook-and-eye fabric, for example, Velcro™. Therefore, the scope of the invention is determined by the following claims.

What is claimed is:

1. A chromatographic assay device for detection of at least one analyte in at least one sample, comprising:
   (a) a first opposable component including:
      (i) at least one sample application zone each containing a matrix of a porous material permeable to the liquid portion of blood but capable of trapping the cellular components of blood; and
      (ii) at least one chromatographic medium each having a first end in operable contact with a corresponding sample application zone and a second end, each chromatographic medium including:
         (A) a detection zone containing an immobilized first reagent; and
         (B) a conjugate zone located between the first end and the detection zone and containing a labeled second reagent in a resolubilizable form; and
   (b) a second opposable component including:
      (i) at least one applicator each corresponding to a sample application zone for applying a wash liquid; and
      (ii) at least one absorber each corresponding to a chromatographic medium;
   wherein when the first and second opposable components are brought into opposition, each applicator is in operable contact with the corresponding sample application zone to apply the wash liquid in the applicator to the sample application zone, and each absorber is in operable contact with the second end of the corresponding chromatographic medium.

2. The chromatographic assay device of claim 1, wherein when the device comprises at least two chromatographic media, the chromatographic media each extends longitudinally and are laterally spaced from each other.

3. The chromatographic assay device of claim 1, wherein the first reagents in all the detection zones are an unlabeled first specific binding partner for the same analyte and the second reagents in all the conjugate zones are a labeled second specific binding partner for the same analyte.

4. The chromatographic assay device of claim 1, wherein when the device comprises at least two chromatographic media, the first and second reagents in at least some of the detection and conjugate zones, respectively, are first and second specific binding partners, respectively, for different analytes.

5. The chromatographic assay device of claim 1, wherein the labels for the labeled second reagents in all detection zones are the same.

6. The chromatographic assay device of claim 5 wherein the label is a colloidal particle label.

7. The chromatographic assay device of claim 6 wherein the colloidal particle label is a colloidal carbon label.

8. The chromatographic assay device of claim 5 wherein the label is a visually detectable label.

9. The chromatographic assay device of claim 1 wherein each analyte is selected from the group consisting of bacterial antigens, protozoan antigens, viral antigens, cell-surface receptor proteins, enzymes, antibodies, hemoglobin, and hormones.

10. The chromatographic assay device of claim 9 wherein each analyte is a hormone.

11. The chromatographic assay device of claim 10 wherein each analyte is selected from the group consisting of human chorionic gonadotropin (hCG), luteinizing hormone (LH), follicle stimulating hormone (FSH), thyroid stimulating hormone (TSH), corticotropin-releasing hormone (CRH), growth hormone-releasing hormone (GHRH), prolactin, human growth hormone (hGH), βlipotropin, corticotropin, βendorphin, calcitonin, parathormone, human placental lactogen (hPL), insulin, glucagon, pancreatic polypeptide (PP), secretin, cholecystokinin-pancreozymin, motilin, vasoactive intestinal peptide, gastric inhibitory peptide, and erythropoietin.

12. The chromatographic assay device of claim 11 wherein each analyte is selected from the group consisting of hCG, TSH, LH, and FSH.

13. The chromatographic assay device of claim 12 wherein each analyte is hCG.

14. The chromatographic assay device of claim 13 wherein the first reagent in each detection zone is a monoclonal antibody specific for the α subunit of hCG and the second reagent in each conjugate zone is a monoclonal antibody specific for the α subunit of hCG and not cross-reactive with luteinizing hormone.

15. The chromatographic assay device of claim 1, wherein each chromatographic medium further includes:
   (C) a validation zone located between the detection zone and the second end and containing an immobilized third reagent, the third reagent binding human antibodies that bind the first or the second reagent.

16. The chromatographic assay device of claim 15, wherein each chromatographic medium further includes:
   (D) a capture zone located between the conjugate zone and the first end and containing a fourth reagent, the fourth reagent binding human antibodies that bind the first or the second reagent.

17. The chromatographic assay device of claim 15, wherein each sample application zone contains a fourth reagent, the fourth reagent binding human antibodies that bind the first or the second reagent.

18. The chromatographic assay device of claim 15, wherein the first opposable component further includes:
   (iii) at least one conductor each in operable contact with a corresponding sample application zone and with the first end of a corresponding chromatographic medium, each conductor containing a fourth reagent, the fourth reagent binding human antibodies that bind the first or the second reagent.

19. The chromatographic assay device of claim 1, wherein each sample application zone is in direct contact with the first end of the corresponding chromatographic medium.

20. The chromatographic assay device of claim 1, further comprising at least one barrier each located between a sample application zone and the corresponding applicator for preventing fluid flow therebetween.

21. The chromatographic assay device of claim 1 wherein each matrix contains a detergent and a chelating agent.

22. The chromatographic assay device of claim 21 wherein the detergent is selected from the group consisting of a polyoxyethylene sorbitan monolaurate, a poloxyethylene sorbitan monooleate, a polyoxyethylene sorbitan monopalmitate, a polyoxyethylene sorbitan monostearate, a polyoxyethylene sorbitan trioleate, a polyethylene glycol fatty alcohol ether, a polyoxyethylene fatty acid ester, t-octylphenoxypolyethoxyethanol and a polyoxyethylene ether.

23. The chromatographic assay device of claim 22 wherein the detergent is a polyoxethylene sorbitan monolaurate or t-octylphenoxypolyethoxyethanol.

24. The chromatographic assay device of claim 21 wherein the chelating agent is selected from the group consisting of EDTA and EGTA.

25. The chromatographic assay device of claim 24 wherein the chelating agent is EDTA.

26. The chromatographic assay device of claim 1 wherein each chromatographic medium further includes a control zone separated from the detection zone.

27. The chromatographic assay device of claim 26 wherein the control zone is located between the detection zone and the second end of the chromatographic medium.

28. The chromatographic assay device of claim 26 wherein the control zone includes an analyte or an analyte analogue immobilized thereto.

29. The chromatographic assay device of claim 26 wherein the control zone includes an immobilized fifth reagent specifically binding the second reagent but not binding the analyte bound by the second reagent.

30. A test kit comprising:
(a) the chromatographic assay device of claim 1; and
(b) a wash liquid packaged in a separate container for application to the applicators of the chromatographic assay device.

* * * * *